(12) United States Patent
Kosomaa et al.

(10) Patent No.: US 11,790,598 B2
(45) Date of Patent: Oct. 17, 2023

(54) THREE-DIMENSIONAL TOMOGRAPHY RECONSTRUCTION PIPELINE

(71) Applicant: NVIDIA Corporation, Santa Clara, CA (US)

(72) Inventors: Onni August Kosomaa, Uusimaa (FI); Jaakko T. Lehtinen, Helsinki (FI); Samuli Matias Laine, Vantaa (FI); Tero Tapani Karras, Helsinki (FI); Miika Samuli Aittala, Helsinki (FI)

(73) Assignee: NVIDIA Corporation, Santa Clara, CA (US)

( * ) Notice: Subject to any disclaimer, the term of this patent is extended or adjusted under 35 U.S.C. 154(b) by 6 days.

(21) Appl. No.: 17/365,574

(22) Filed: Jul. 1, 2021

(65) Prior Publication Data
US 2022/0189100 A1    Jun. 16, 2022

Related U.S. Application Data

(60) Provisional application No. 63/126,025, filed on Dec. 16, 2020.

(51) Int. Cl.
*G06T 15/08* (2011.01)
*G06T 11/00* (2006.01)
(Continued)

(52) U.S. Cl.
CPC .......... *G06T 15/08* (2013.01); *G06N 3/045* (2023.01); *G06T 11/006* (2013.01); *G16H 30/40* (2018.01); *G06T 2210/41* (2013.01)

(58) Field of Classification Search
None
See application file for complete search history.

(56) References Cited

U.S. PATENT DOCUMENTS 10,970,518 B1\* 4/2021 Zhou ............... G06T 15/08
2006/0119608 A1\* 6/2006 Prokopenko ........ G06T 15/04
345/586

(Continued)

OTHER PUBLICATIONS

Berg et al., "Generation of ground truth images to validate micro-CT image-processing pipelines," The Leading Edge 37.6 (2018): 412-420 (Year: 2018).*

(Continued)

*Primary Examiner* — Anh-Tuan V Nguyen
(74) *Attorney, Agent, or Firm* — Leydig, Voit & Mayer, Ltd.

(57) ABSTRACT

A three-dimensional (3D) density volume of an object is constructed from tomography images (e.g., x-ray images) of the object. The tomography images are projection images that capture all structures of an object (e.g., human body) between a beam source and imaging sensor. The beam effectively integrates along a path through the object producing a tomography image at the imaging sensor, where each pixel represents attenuation. A 3D reconstruction pipeline includes a first neural network model, a fixed function backprojection unit, and a second neural network model. Given information for the capture environment, the tomography images are processed by the reconstruction pipeline to produce a reconstructed 3D density volume of the object. In contrast with a set of 2D slices, the entire 3D density volume is reconstructed, so two-dimensional (2D) density images may be produced by slicing through any portion of the 3D density volume at any angle.

20 Claims, 18 Drawing Sheets

(51) Int. Cl.
*G16H 30/40* (2018.01)
*G06N 3/045* (2023.01)

(56) References Cited

U.S. PATENT DOCUMENTS

| | | | | |
|---|---|---|---|---|
| 2007/0217666 | A1* | 9/2007 | Gal | G01T 1/1642 382/131 |
| 2008/0058639 | A1* | 3/2008 | Sakaida | G16H 30/40 600/425 |
| 2009/0274354 | A1* | 11/2009 | Ng | A61B 6/4028 382/131 |
| 2013/0294568 | A1* | 11/2013 | Lee | A61B 6/025 378/4 |
| 2015/0253263 | A1* | 9/2015 | Feser | G01N 23/2206 378/6 |
| 2015/0325010 | A1* | 11/2015 | Bedford | G01V 5/0066 378/57 |
| 2018/0018757 | A1* | 1/2018 | Suzuki | G06T 3/4053 |
| 2018/0204305 | A1* | 7/2018 | Wang | G06T 11/006 |
| 2019/0164288 | A1* | 5/2019 | Wang | G06T 5/005 |
| 2019/0333219 | A1* | 10/2019 | Xu | G06N 3/088 |
| 2019/0369190 | A1* | 12/2019 | Ye | G06N 20/10 |
| 2020/0273214 | A1* | 8/2020 | Xu | G06N 3/08 |
| 2020/0279411 | A1* | 9/2020 | Atria | G06T 11/006 |
| 2021/0110533 | A1* | 4/2021 | Viti | G06N 3/082 |
| 2021/0192809 | A1* | 6/2021 | Paysan | G06N 3/08 |
| 2021/0304402 | A1* | 9/2021 | Morgas | G06N 20/00 |
| 2021/0364426 | A1* | 11/2021 | Yang | G06T 11/005 |
| 2021/0374961 | A1* | 12/2021 | Wang | G06T 5/002 |
| 2021/0393229 | A1* | 12/2021 | Shen | A61B 6/032 |
| 2022/0036605 | A1* | 2/2022 | Riddell | A61B 6/032 |

OTHER PUBLICATIONS

Bippus et al., "Projector and backprojector for iterative CT reconstruction with blobs using CUDA," 11th International Meeting on Fully Three-Dimensional Image Reconstruction in Radiology and Nuclear Medicine, Potsdam, Germany, Jul. 11-15, 2011 (Year: 2011).*

Lehtinen, J., et al., "Noise2Noise: Learning Image Restoration Without Clean Data," ICML, arXiv:1803.04189v3, 2018.

Ronneberger, O., et al., "U-Net: Convolutional Networks for Biomedical Image Segmentation," MICCAI, Computer Science Department and BIOSS Centre for Biological Signalling Studies, University of Freiburg, Germany, 2015.

Wang, G., et al., "Approximate and exact cone-beam reconstruction with standard and non-standard spiral scanning," Phys Med Biol. 52(6), 2007. (Abstract).

He, J., et al., "Radon Inversion via Deep Learning," arXiv:1808:03015, Department of Biomedical Engineering, Southern Medical University, Guangzhou, China, [2018].

Turbell, H., "Cone-Beam Reconstruction Using Filtered Backprojection," Linkoping Studies in Science and Technology Dissertation No. 672, [2001].

Yedder, H., et al., "Deep Learning for Biomedical Image Reconstruction: A Survey," arXiv: 2002.12351, Feb. 26, 2020.

* cited by examiner

THREE-DIMENSIONAL TOMOGRAPHY RECONSTRUCTION PIPELINE

CLAIM OF PRIORITY

This application claims the benefit of U.S. Provisional Application No. 63/126,025 titled "Three-Dimensional Reconstruction for Computed Tomography," filed Dec. 16, 2020, the entire contents of which is incorporated herein by reference.

BACKGROUND

Tomographic images generated from x-ray machines, such as conic beam scanning machines, provide valuable diagnostic information. Typically, the tomographic images are noisy which interferes with or reduces the diagnostic value of the tomographic images. While increasing the x-ray radiation dose reduces the noise, increasing the dose is detrimental to the subject being scanned. There is a need for addressing these issues and/or other issues associated with the prior art.

SUMMARY

Embodiments of the present disclosure relate to a three-dimensional (3D) tomography reconstruction pipeline. Systems and methods are disclosed that construct a 3D density volume from tomography images (e.g., x-ray images). The tomography images are projection images that capture all structures of a subject or object (e.g., human body) between a beam source and imaging sensor. The beam effectively integrates along a path through the object producing a tomography image at the imaging sensor, where each pixel represents attenuation along the path. In an embodiment, a 3D reconstruction pipeline includes a first neural network model, a fixed function backprojection unit, and a second neural network model. Given information of the capture environment, the tomography images are processed by the 3D reconstruction pipeline to produce a reconstructed 3D density volume of the object. In contrast with a set of two-dimensional (2D) slices, the entire 3D density volume is reconstructed, so 2D density images may be computed by slicing through any portion of the 3D density volume at any angle.

A method, computer readable medium, and system are disclosed for 3D tomography reconstruction. The method includes the steps of processing tomography images by a first neural network to produce at least one channel of 2D features for each tomography image and computing 3D features by backprojecting the at least one channel of 2D features for the tomography images according to characteristics of a physical environment used to capture the tomography images. The 3D features are processed by a second neural network to produce a 3D density volume corresponding to the tomography images.

A method, computer readable medium, and system are disclosed for training a 3D tomography reconstruction neural network system. The method includes the steps of processing 2D tomography images of an object by the neural network system, according to parameters, to produce a 3D density volume for the object, where the 2D tomography images are generated by a physical capture environment. The 3D density volume is projected, based on characteristics of the capture environment, to produce simulated tomography images corresponding to the 2D tomography images and the parameters of the neural network system are adjusted to reduce differences between the simulated tomography images and the 2D tomography images.

BRIEF DESCRIPTION OF THE DRAWINGS

The present systems and methods for a 3D tomography reconstruction pipeline are described in detail below with reference to the attached drawing figures, wherein.

DETAILED DESCRIPTION

Figure 1A:
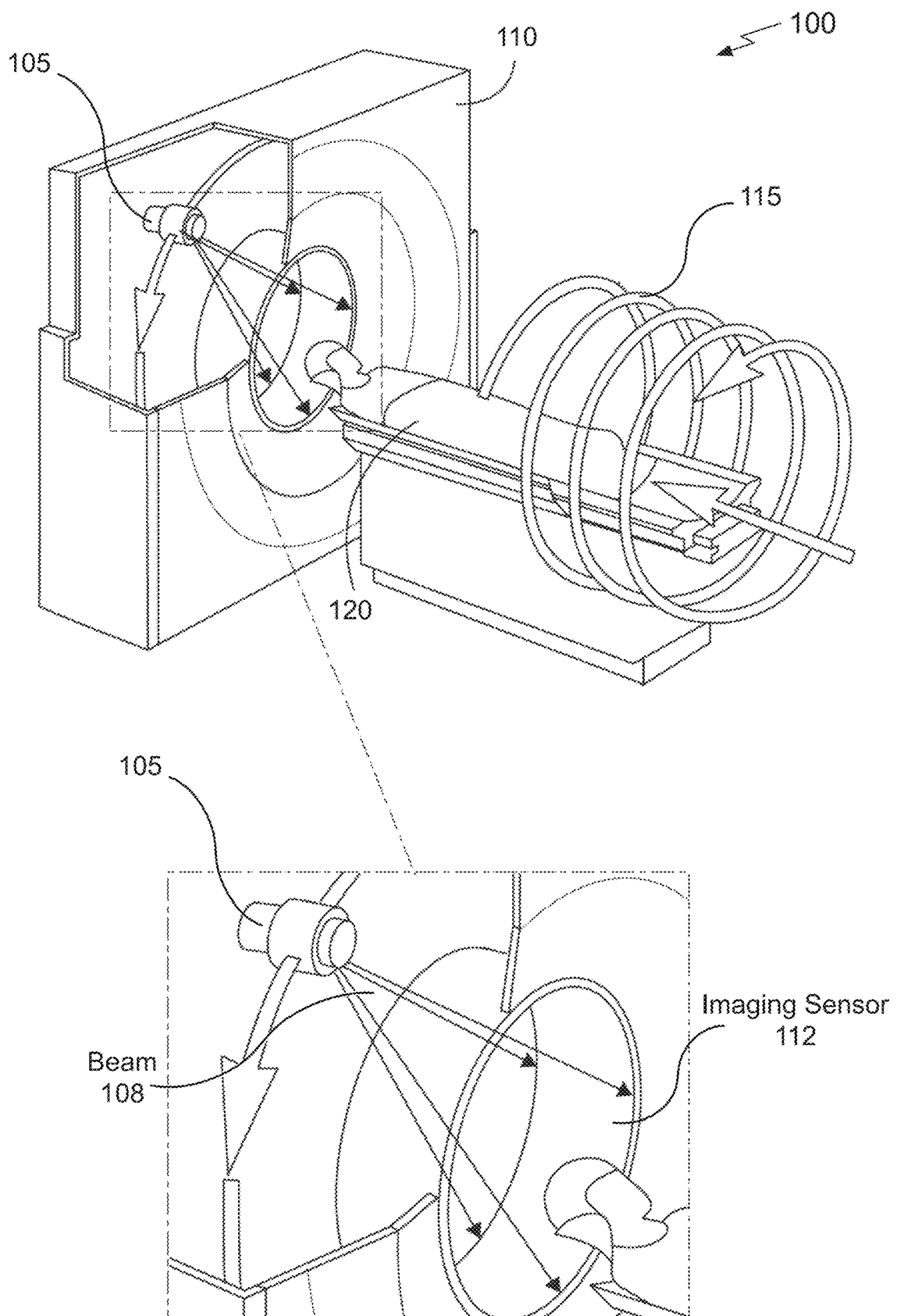
FIG. 1A illustrates an environment for generating tomography images suitable for use in implementing some embodiments of the present disclosure.

Systems and methods are disclosed related to 3D tomography reconstruction. In an embodiment, a 3D density volume (model) is constructed from tomography images (e.g., x-ray images). The tomography images are projection images that capture all structures of an object (e.g., human body) between a beam source and imaging sensor. In an embodiment, the imaging sensor comprises multiple rows of detector elements. The beam effectively integrates along a path through the object producing a tomography image at the imaging sensor, where each pixel represents attenuation along the path, producing a 2D projection image, such as an x-ray image. In an embodiment, a 3D reconstruction pipeline includes a first neural network model, a fixed function backprojection unit, and a second neural network model. Given information for the capture environment, the tomography images are processed by the 3D reconstruction pipeline to produce a reconstructed 3D density volume of the object. In contrast with a set of 2D slices, the entire 3D density volume is reconstructed, so 2D density images may be computed by slicing through any portion of the 3D density volume at any angle.

In the context of the following description, several terms are defined as follows.
- Tomography image: 2D projection image of a 3D volume of an object, subject, or body that is generated by a tomography machine.
- 3D density volume: Reconstructed 3D model generated from tomography images.
- Simulated tomography images: Simulated projections or 2D density images generated from the 3D density volume to simulate real tomography images.
- Slice: Planar portion of the 3D density volume, such as a 2D density image corresponding to a 2D plane slicing through or intersecting the 3D density volume.

A slice is a reconstructed image at a 2D plane that illustrates content within the body at the plane without the "obscuring" projections of material between the x-ray source and the content at the plane. Conventional backprojection techniques reconstruct individual 2D slices from the tomography images, using pixels selected based on the beam and slice plane. In contrast, the entire 3D density volume is reconstructed from the tomography images and individual slices may be generated from the 3D density volume.

In an embodiment, projection images (or 2D features generated from the projection image) used during the 3D tomography reconstruction to generate the 3D density volume are pre-filtered. Pre-filtering a projection image provides a set of projection images at varying resolutions, such as a MIP (multum in parvo) map including varying levels of detail. Generating the set of pre-filtered projection images is efficient and techniques such as bilinear and/or trilinear filtering may be used to sample one or more of the different pre-filtered projection images in the set to reduce aliasing of backprojected data.

Systems and methods are disclosed related to end-to-end training for a 3D tomography reconstruction pipeline. In contrast to conventional systems that employ supervised training, self-supervised training may be used to train the 3D tomography reconstruction pipeline. Conventional supervised training requires 2D tomography images and corresponding ground truth density data as training data. However, perfectly noise-free ground truth density data is not available. Rather than attempt to train the reconstruction pipeline using estimated 3D density volumes obtained by some other technique, the self-supervised training instead generates simulated tomography images from the 3D density volume output by the reconstruction pipeline. The simulated 2D input tomography images may be compared with the input tomography images used to generate the 3D density volume. Parameters of the 3D tomography reconstruction pipeline may be learned to reduce differences between the simulated and input tomography images.

FIG. 1A illustrates an environment 100 for generating tomography images suitable for use in implementing some embodiments of the present disclosure. Different types of machines capture the tomography images according to a physical environment using different mechanisms and beam scanning paths. For example, a first machine (not shown) may project planar (e.g., parallel) beams. A second machine, such as a machine 110 may include a beam emitter 105 that projects a conical or pyramidal shaped beam 108 onto a circular imaging sensor 112 positioned within the machine 110. In an embodiment, the imaging sensor 112 is flat instead of curved. In an embodiment, the imaging sensor 112 rotates in coordination with the beam source 105. In an embodiment, the imaging sensor 112 rotates at the same speed as the beam source 105.

The machine 110 moves the beam 108 in a circle around an object 120. The object 120 is continuously shifted through the circular imaging sensor 112 resulting in a spiral beam scanning path 115. Another machine (not shown) may alternate between rotating the beam in a circle around an object and shifting the object through the circle, generating several disconnected circular tomography images at different points along the length of the object.

The beam 108 moves along the beam scanning path 115 and forms projection images at the imaging sensor 112. Given information specific to the capture environment 100, the tomography images may be backprojected to produce a reconstructed 2D density image or 3D density volume of the object. Characteristics of the capture environment 100 may include specific geometry, positions, and/or orientations of the beam emitter 105, the beam scanning path 115, the imaging sensor 112, the beam 108, and the like.

Figure 1B:
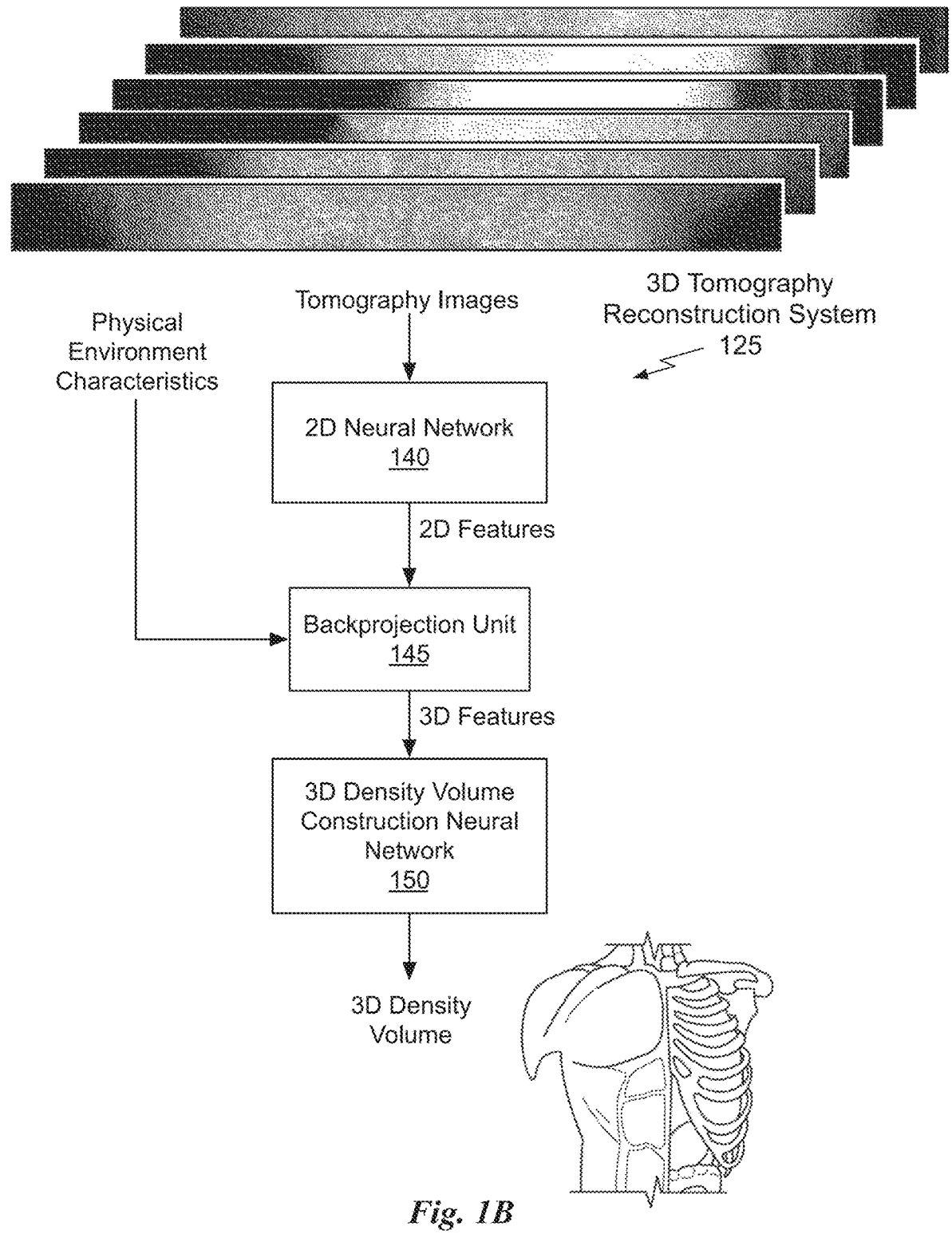
FIG. 1B illustrates a block diagram of an example 3D tomography reconstruction system suitable for use in implementing some embodiments of the present disclosure.

FIG. 1B illustrates a block diagram of an example 3D tomography reconstruction system 125 suitable for use in implementing some embodiments of the present disclosure. It should be understood that this and other arrangements described herein are set forth only as examples. Other arrangements and elements (e.g., machines, interfaces, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory. Furthermore, persons of ordinary skill in the art will understand that any system that performs the operations of the 3D tomography reconstruction system 125 is within the scope and spirit of embodiments of the present disclosure.

The 3D tomography reconstruction system 125 is a 3D reconstruction pipeline that includes a 2D neural network 140, a fixed function backprojection unit 145, and a 3D density volume construction neural network 150. The 2D neural network 140 receives the 2D tomography images and generates at least one channel of 2D features (per pixel) for each tomography image. The tomography images are typically quite noisy (appearing grainy, coarsely sampled, and/or including visual artifacts). Although the noise may be reduced by increasing the x-ray radiation dose used to capture the tomography images, increasing the x-ray radiation may be detrimental to the health of the subject. When conventional backprojection techniques are used to generate a 2D density image (slice), the noise present in the tomography images is also backprojected—resulting in a noisy 2D density image. The 2D neural network 140 reduces the noise when processing the tomography images, producing a 3D density volume with reduced noise. The ability to reduce the noise may beneficially allow lower x-ray doses.

First, the tomography images are each separately processed independently by one or more 2D neural networks 140 to generate at least one channel of 2D features. In an embodiment, multiple channels of 2D features are generated to provide higher dimensional data. The 2D tomography images inherently include 3D information because they are projections with per-pixel attenuation values. Therefore, each channel of the 2D features that is generated encodes the 3D information represented in the tomography image.

The backprojection unit 145 "smears" the 2D features for each tomography image along the beam 108 used to capture the tomography image to generate 3D features. In an embodiment, the 3D features include voxels and associated attributes of a 3D density volume. The smearing is conceptually illustrated in FIGS. 2A and 2B. The computations performed by the backprojection unit 145 may vary based on the specific capture environment, such as the capture environment 100. Having 2D tomography images captured from a variety of different angles enables recovery of the 3D data. The 2D features for each tomography image may be backprojected independently (and in parallel) to compute the voxel attributes. Importantly, the 2D features for multiple images may contribute to a single voxel. Compared with conventional techniques that generate a single slice, more pixels of the tomography images are typically utilized during the backprojection calculation to produce the 3D density volume. In an embodiment, backprojecting includes high pass filtering and 2D image lookup operations. In another embodiment, backprojecting may also include raycasting operations. A gather-based backprojection approach loops over the 3D voxels and performs lookups from the 2D tomography images. A scatter-based backprojection approach loops over the 2D pixels and performs ray casts to the 3D voxels. Backprojection techniques are described in detail in H. Turbell, "Cone-beam reconstruction using filtered backprojection" Ph.D. thesis, University of Linköping, Sweden, February 2001, the entire contents of which is incorporated herein by reference.

The 2D neural network 140 and the 3D density volume construction neural network 150 are each learned filters implemented using neural network models. In contrast, the backprojection unit 145 performs fixed function operations and does not require training. However, in an embodiment, the 2D neural network 140 and/or the 3D density volume construction neural network 150 is replaced with a fixed function filter.

The 3D density volume construction neural network 150 processes the 3D features (voxels and attributes) to generate the 3D reconstruction of the subject as a 3D density volume. The 3D density volume in FIG. 1B is a conceptual representation of a torso that has the outermost layer and portions of underlying layers removed to illustrate that the 3D density volume represents the internal structure of the subject in contrast with a 3D mesh that consists of only the outermost layer.

During processing, the 3D density volume construction neural network 150 corrects reconstruction errors introduced in the backprojection calculation. The 3D density volume construction neural network 150 may reduce remaining noise present in the 3D features, producing a 3D density volume with reduced noise. An advantage of reconstructing the entire 3D density volume is that 2D density images may be produced by slicing through any portion of the 3D density volume at any angle.

Conventional techniques process the 2D tomography images to generate a single slice for a specific intersecting plane (e.g., cross section). For example, specific intersecting x,y planes may correspond to different z coordinate values on the z axis along which the subject is shifted through the scanning machine. While multiple slices may be generated by the conventional techniques, each slice is individually reconstructed.

More illustrative information will now be set forth regarding various optional architectures and features with which the foregoing framework may be implemented, per the desires of the user. It should be strongly noted that the following information is set forth for illustrative purposes and should not be construed as limiting in any manner. Any of the following features may be optionally incorporated with or without the exclusion of other features described.

Figure 1C:
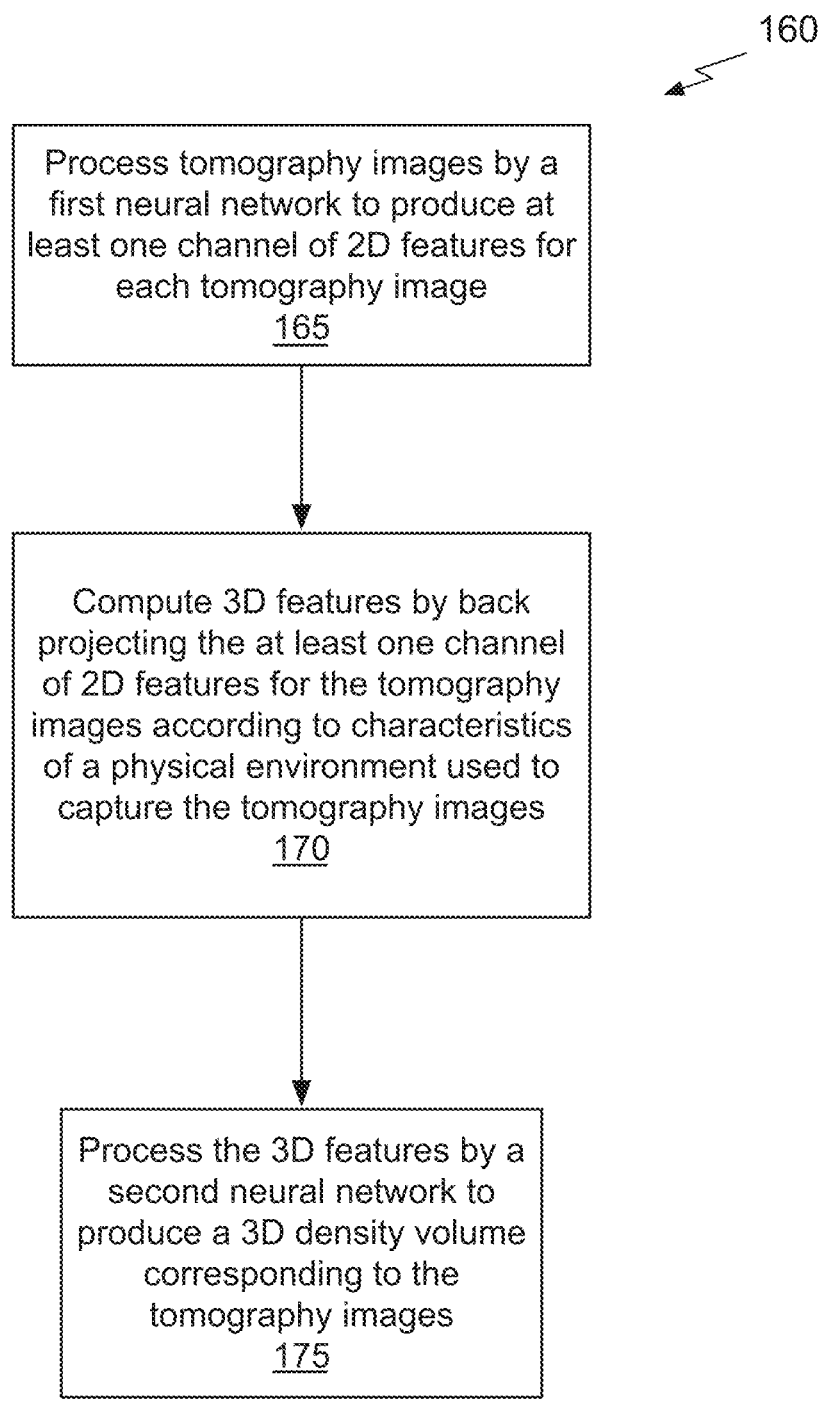
FIG. 1C illustrates a flowchart of a method for 3D tomography reconstruction suitable for use in implementing some embodiments of the present disclosure.

FIG. 1C illustrates a flowchart of a method 160 for 3D tomography reconstruction suitable for use in implementing some embodiments of the present disclosure. Each block of method 160, described herein, comprises a computing process that may be performed using any combination of hardware, firmware, and/or software. For instance, various functions may be carried out by a processor executing instructions stored in memory. The method may also be embodied as computer-usable instructions stored on computer storage media. The method may be provided by a standalone application, a service or hosted service (standalone or in combination with another hosted service), or a plug-in to another product, to name a few. In addition, method 160 is described, by way of example, with respect to the system of FIG. 1B. However, this method may additionally or alternatively be executed by any one system, or any combination of systems, including, but not limited to, those described herein. Furthermore, persons of ordinary skill in the art will understand that any system that performs method 160 is within the scope and spirit of embodiments of the present disclosure.

At step 165, tomography images are processed by a first neural network to produce at least one channel of 2D features for each tomography image. In an embodiment, the first neural network is the 2D neural network 140. The tomography images consist of an attenuation value for each pixel, wherein the 2D features may include one or more feature values (channels) associated with each pixel.

At step 170, 3D features are computed by backprojecting the at least one channel of 2D features for the tomography images. The at least one channel of 2D features are backprojected according to characteristics of a physical environment used to capture the tomography images. In an embodiment, the backprojection unit 145 computes the 3D features. In an embodiment, the 3D features are voxels and associated attributes. In an embodiment, the physical environment used to capture the tomography images comprises a conical spiral computerized tomography machine. In an embodiment, the backprojecting includes computing a projected footprint for a voxel or pixel and accessing one or more pre-filtered versions of the tomography images or 2D features according to at least one dimension of the projected footprint. In an embodiment, such as when conventional slice reconstruction is performed, the projected footprint is computed for a pixel. Conceptually, a 3D voxel of the 3D features corresponds to a 2D pixel on a slice.

At step 175, the 3D features are processed by a second neural network to produce a 3D density volume corresponding to the tomography images. In an embodiment, the second neural network is the 3D density volume construction neural network 150. In an embodiment, noise present in the tomography images is reduced in the 3D density volume. In an embodiment, the 3D density volume corresponds to a portion of a human body.

Figure 1D:
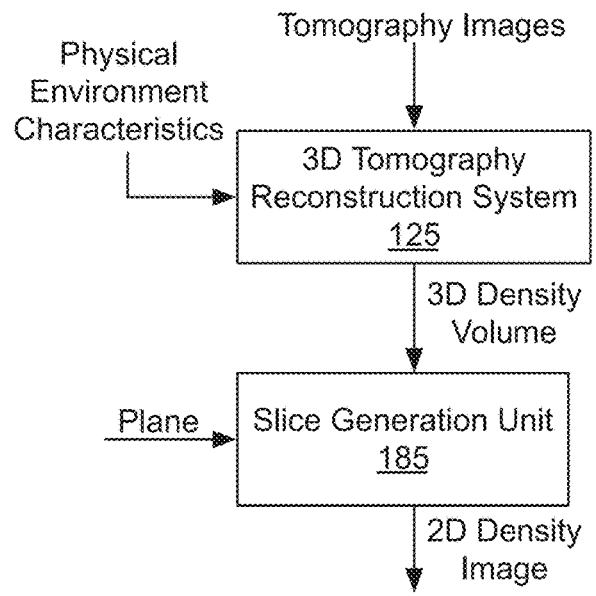
FIG. 1D illustrates a block diagram of an example 2D density image generation system including the 3D tomography reconstruction system of FIG. 1B suitable for use in implementing some embodiments of the present disclosure.
Figure 1D:
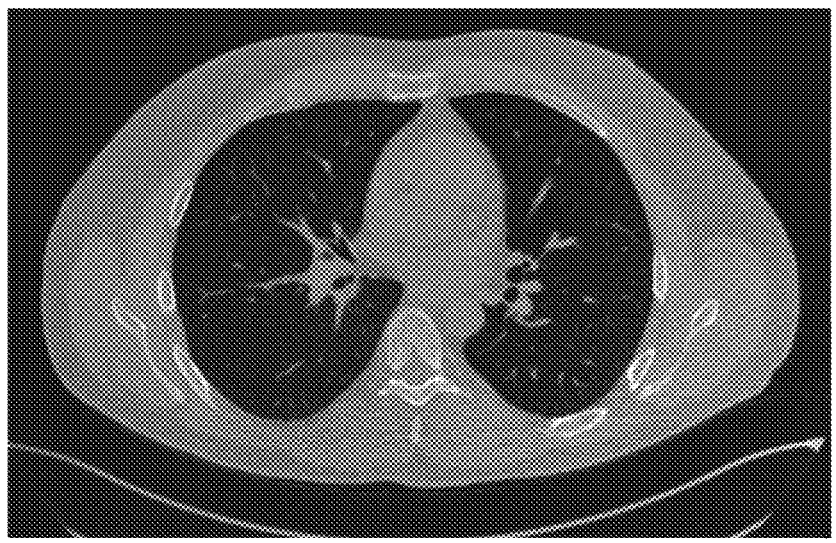
Figure 1D:
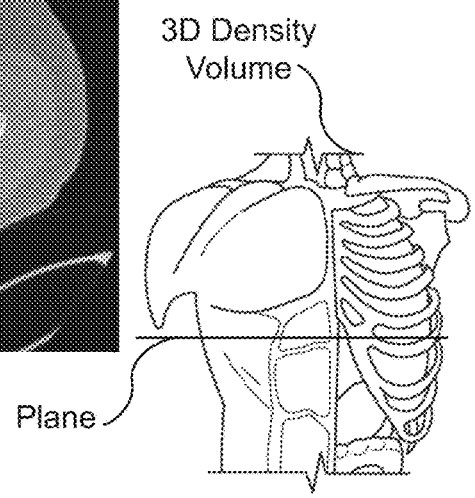

FIG. 1D illustrates a block diagram of an example 2D density image generation system including the 3D tomography reconstruction system 125 of FIG. 1B suitable for use in implementing some embodiments of the present disclosure. A slice generation unit 185 processes the 3D density volume according to an intersecting plane to generate a 2D density image. The intersecting plane may be defined at any angle relative to a coordinate system corresponding to the 3D density volume.

Figure 1E:
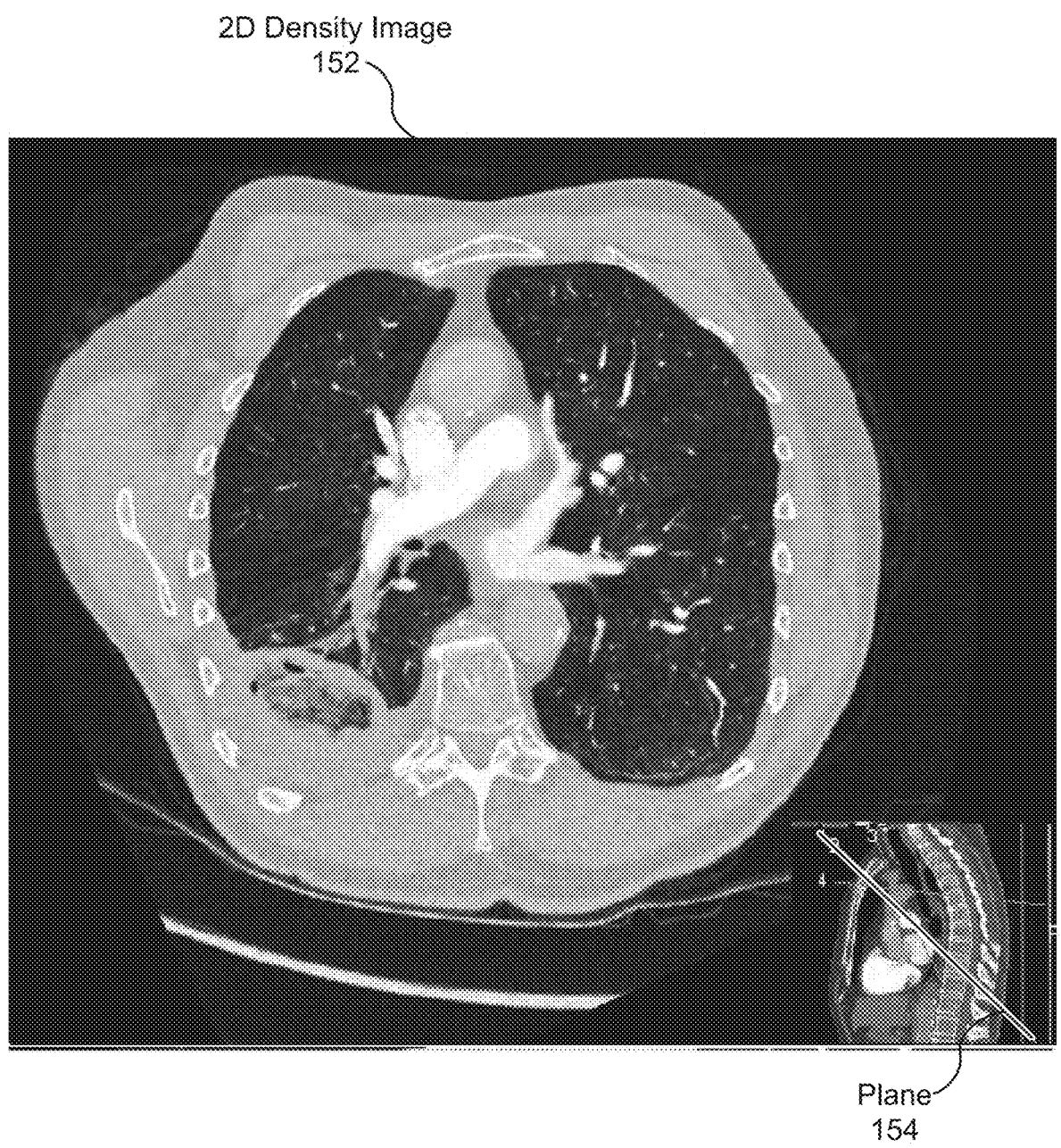
FIG. 1E illustrates a 2D density image generated from a reconstructed 3D density volume, in accordance with an embodiment.

FIG. 1E illustrates a 2D density image 152 generated from a reconstructed 3D density volume, in accordance with an embodiment. A plane 154 is defined for generation of the 2D density image 152 from a reconstructed 3D density volume of a human torso. As shown in FIG. 1E, the plane 154 intersects the reconstructed 3D density volume in a diagonal orientation from approximately the collarbone to the middle of the spine to produce the 2D density image 162.

Figure 1F:
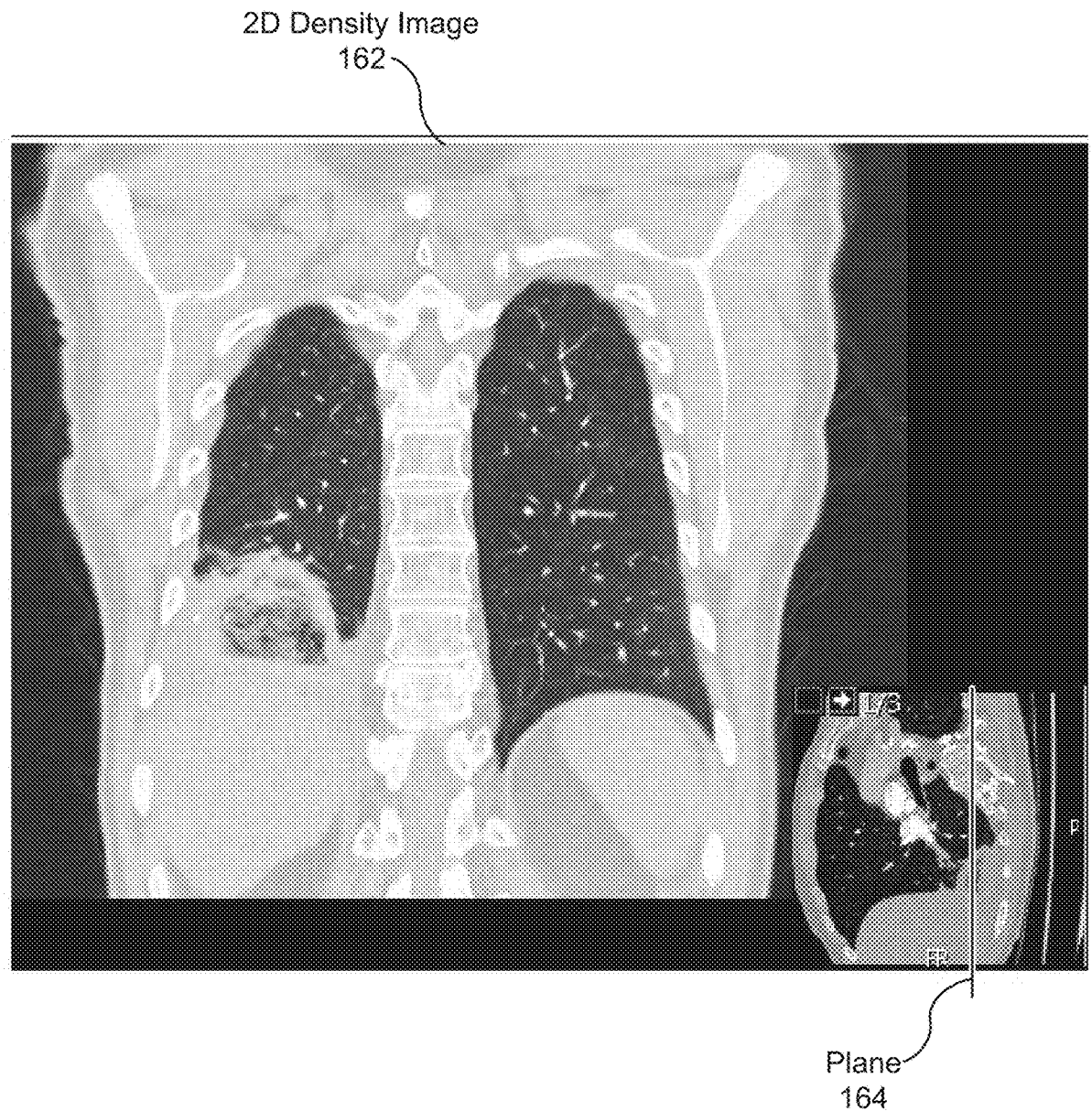
FIG. 1F illustrates another 2D density image generated from the reconstructed 3D density volume, in accordance with an embodiment.

FIG. 1F illustrates another 2D density image 162 generated from the reconstructed 3D density volume, in accordance with an embodiment. A plane 164 is defined for generation of the 2D density image 162 from the reconstructed 3D density volume of the human torso. As shown in FIG. 1F, the plane 164 intersects the reconstructed 3D density volume in a vertical orientation approximately aligned with the spine to produce the 2D density image 162.

Figure 1G:
FIG. 1G illustrates yet another 2D density image generated from the reconstructed 3D density volume, in accordance with an embodiment.

FIG. 1G illustrates yet another 2D density image 172 generated from the reconstructed 3D density volume, in accordance with an embodiment. A plane 174 is defined for generation of the 2D density image 172 from the reconstructed 3D density volume of the human torso. As shown in FIG. 1G, the plane 174 intersects the reconstructed 3D density volume in a vertical orientation through the chest and offset to the left from the spine to produce the 2D density image 172.

Figure 2A:
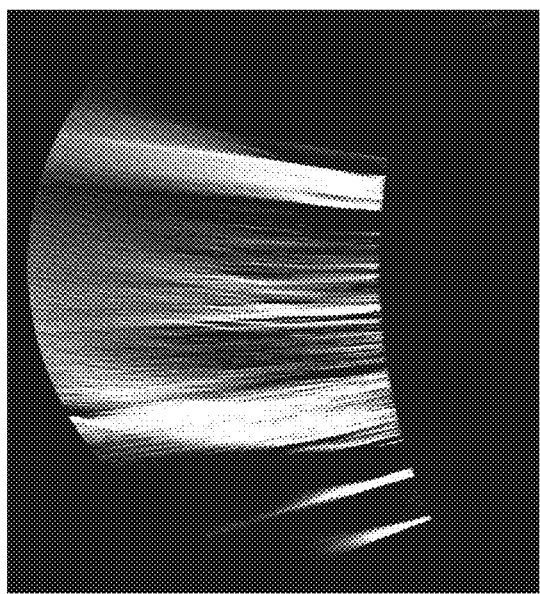
FIG. 2A is a conceptual diagram illustrating backprojection of 2D tomography images that contribute to a 3D density volume, in accordance with an embodiment.
Figure 2A:
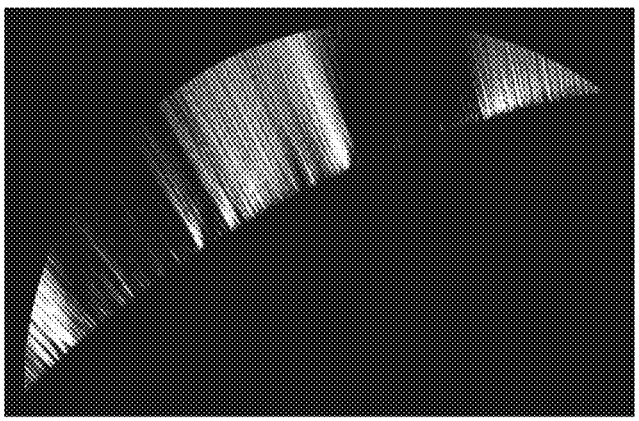
Figure 2A:
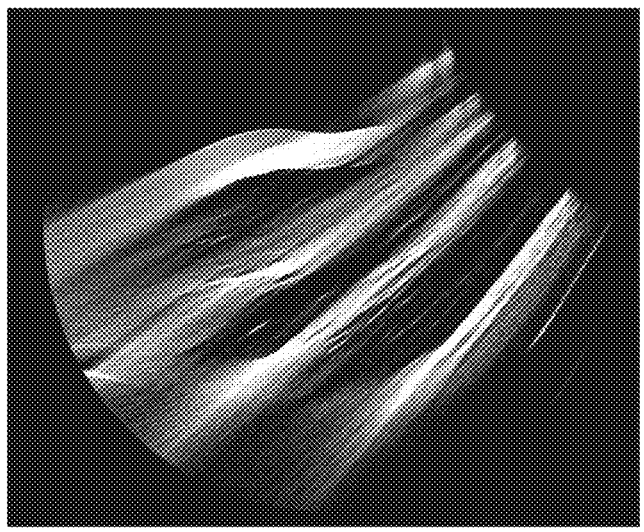
Figure 2A:
Figure 2B:
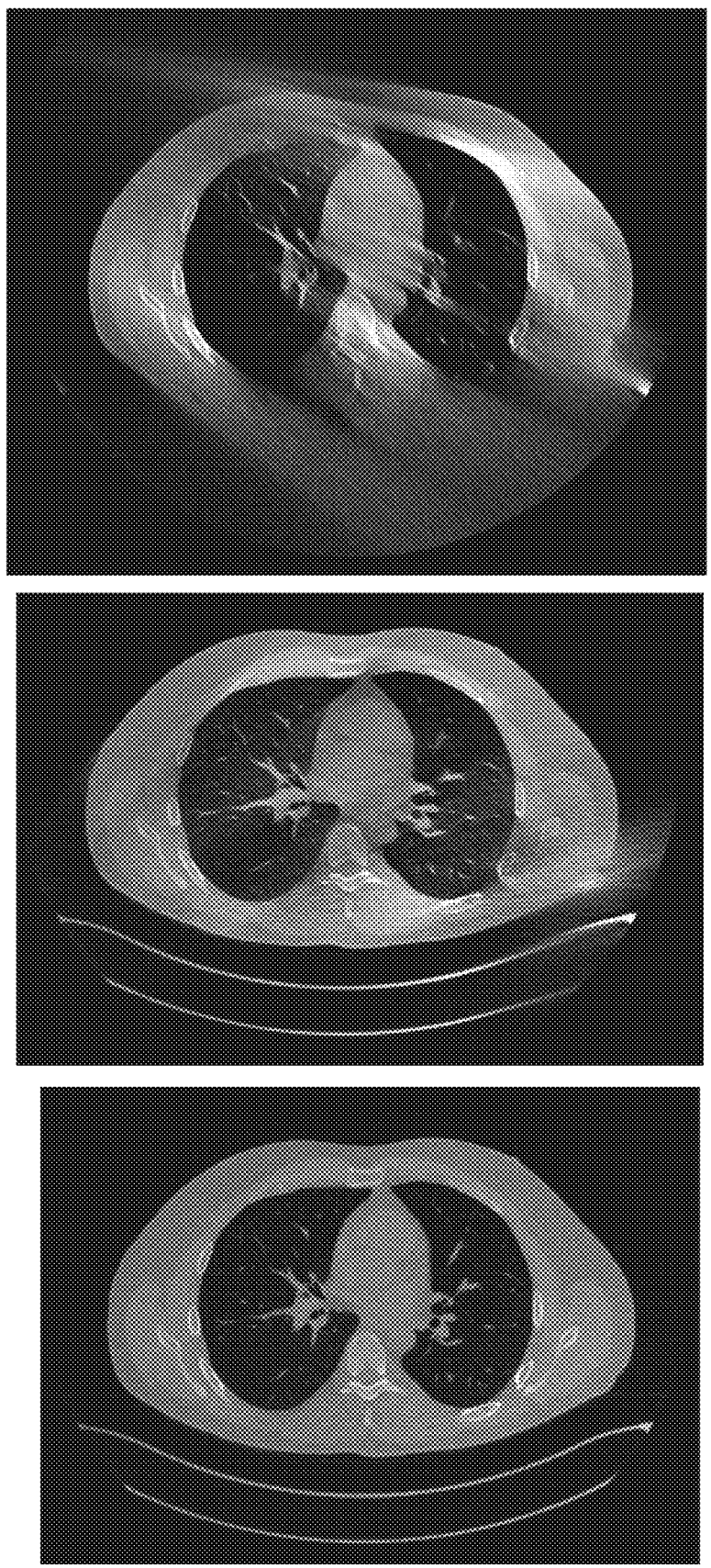
FIG. 2B is a conceptual diagram illustrating backprojection of additional 2D tomography images that also contribute to the 3D density volume, in accordance with an embodiment.

FIGS. 2A and 2B are conceptual diagrams illustrating backprojection of 2D tomography images that contribute to a 3D density volume, in accordance with an embodiment. In an embodiment, 2D features are generated by the 2D neural network 140 for the tomography images and the 2D features are effectively smeared backwards along the path of the corresponding beam by the backprojection unit 145 to produce the 3D features. In an embodiment, each backprojected 2D tomography image influences 3D voxels in the region corresponding to the beam used to produce the projected 2D tomography image. For the purposes of visualization, partial 2D density images and a complete accumulated 2D density image is used to represent the 3D features corresponding to a slice of the 3D density volume.

Figure 2C:
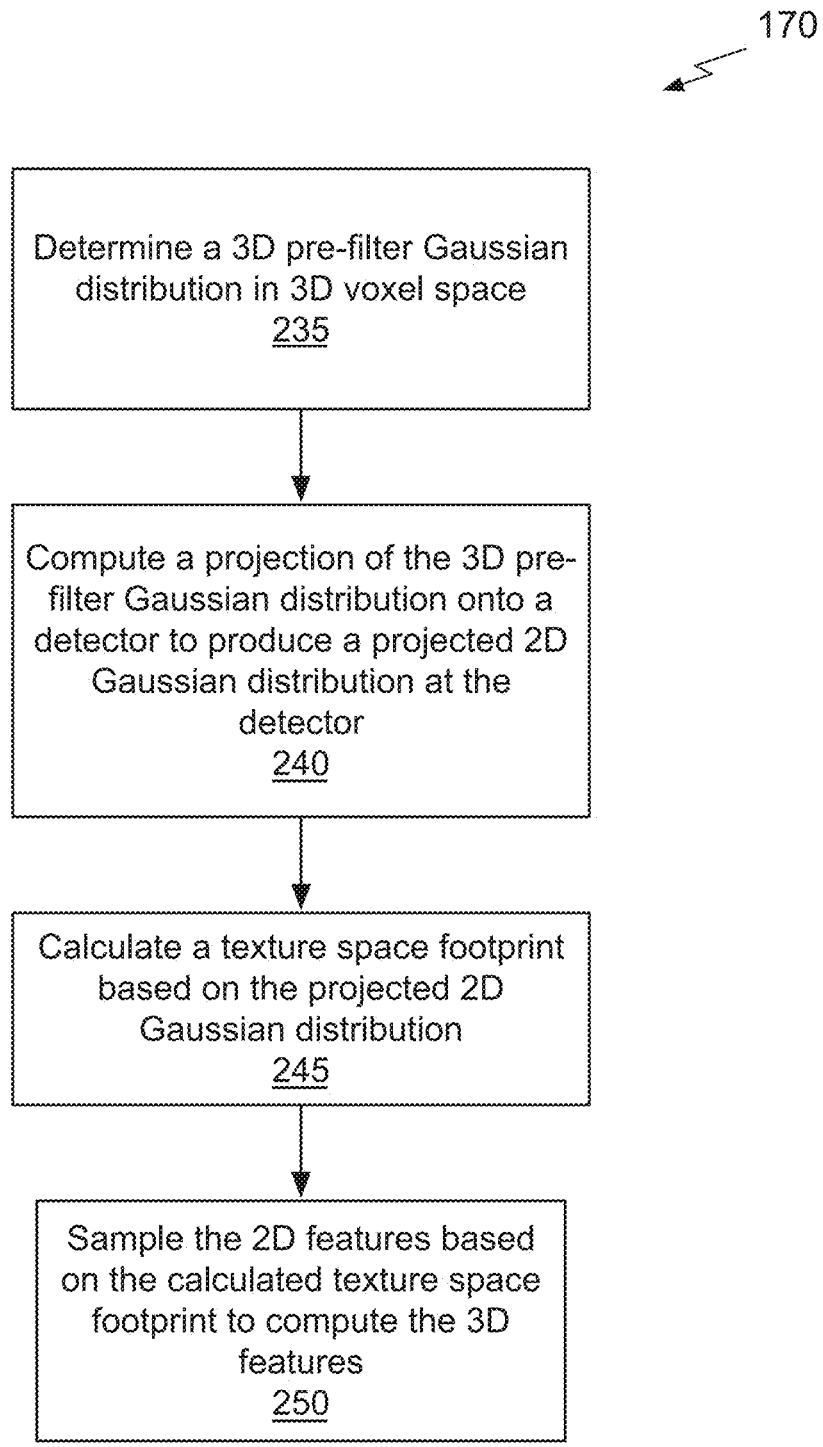
FIG. 2C illustrates a flowchart of a method for performing a step of the flowchart shown in FIG. 1B suitable for use in implementing some embodiments of the present disclosure.

FIG. 2C illustrates a flowchart of a method for performing step 170 of the method 160 shown in FIG. 1B that is suitable for use in implementing some embodiments of the present disclosure. As previously described, at step 170, 3D features are computed by backprojecting the at least one channel of 2D features for the tomography images.

At step 235, a 3D pre-filter Gaussian distribution in 3D voxel space is determined. The 3D pre-filter Gaussian distribution may be determined based on properties of the voxel grid and input tomography images such as resolution, pixel/voxel spacing, or characteristics of the physical environment, such as the capture environment 100 and/or detector, such as the imaging sensor 112. Importantly, the content of the images is not used to determine the 3D pre-filter Gaussian distribution. In an embodiment, the pre-filter Gaussian distribution is sized according to a spacing of the 3D voxels. At step 240, a projection of the 3D pre-filter Gaussian distribution onto detector, is computed to produce a projected 2D Gaussian distribution at the detector. In an embodiment, the projection is computed according to characteristics of the physical environment used to capture the tomography images (i.e., the capture environment).

At step 245, a texture space footprint is calculated based on the projected 2D Gaussian distribution. In an embodiment, the texture space for texture data is equivalent to the 2D feature space for the at least one channel of 2D features. At step 250, the 2D features generated for the tomography images are sampled based on the calculated texture space footprint to compute the 3D features. In an embodiment, texture coordinates and associated filtering information are determined for sampling the 2D features. Pre-filtering 2D features for a projection image provides a set of 2D features at varying resolutions. Generating the set of pre-filtered 2D features is efficient and techniques such as bilinear and/or trilinear filtering may be used to sample one or more of the different pre-filtered 2D features in the set to reduce aliasing of backprojected data. Conventional backprojection techniques typically sample the 2D tomography images at the highest resolution and compute backprojected data for any size footprint using filtering. For example, when nearest neighbor sampling is used, aliasing may cause line artifacts in a backprojected volume generated using conventional techniques. Although the pre-filtering technique is described in the context of the 3D tomography reconstruction system 125, the pre-filtering technique may be used to improve the quality of 2D density images produced by conventional backprojection-based systems.

In an embodiment, one or more of the steps 235, 240, 245, and 250 are performed in parallel for at least a portion of the voxels in the 3D features. In an embodiment, one or more of the steps 235, 240, 245, and 250 are performed in parallel for the 2D features of at least a portion of the tomography images. In contrast with conventional techniques, the backprojection operation performed by step 170 directly generates 3D features of the 3D density volume by backprojecting the beams corresponding to each pixel in the tomography images based on the characteristics of the capture environment. Multiple pixels from different 2D tomography images contribute to the 3D features. The characteristics may be used to determine an origin and direction of each beam. Therefore, approximations relied on by conventional backprojection techniques, such as re-binning of spiral-trajectory conical measurements into flat Z planes, may be avoided. Furthermore, reconstruction errors caused by the combination of spiral-trajectory and backprojection may be corrected by the 3D density volume construction neural network 150.

Overall, generation of the 3D density volume enables computation of 2D density images for any plane that intersects the 3D density volume. Because the 3D tomography reconstruction system 125 does not necessarily propagate noise present in the tomography images to the 3D density volume, the radiation dose used to capture the tomography images may be reduced.

End-to-End Training for a Three-Dimensional Tomography Reconstruction Pipeline Conventional supervised learning techniques require a reference 3D density volume as a guide or ground truth output for use during training. 3D tomography reconstruction is somewhat unique in that the reference 3D density volume cannot be measured directly. For example, providing reference density data for a human body requires a physical sampling of the human body which is impractical if not impossible. Relying on reference 3D density volumes constructed from tomography images using conventional systems do not qualify as true references due to the noise and other artifacts present in defective reference 3D density volumes. A neural network-based system being trained would simply learn to reproduce the artifacts present in the defective reference 3D density volumes rather than generating higher-quality 3D density volumes.

For the best results, supervised training should use 2D tomography images that are representative of the inputs that are seen in production use (i.e., when the trained system is deployed in a clinical setting) and corresponding ground truth 3D density data. Therefore, the 2D tomography images typically include noise. Increasing the radiation dose may reduce the noise in the 2D tomography images, but unfortunately, perfectly noise-free ground truth 3D density data is not available. If noise-free or low-noise 2D tomography images are available, different types and amounts of noise and/or other corruptions may be introduced in the 2D tomography images to train the system for deployment in a clinical setting.

The 3D tomography reconstruction system 125 may be trained using self-supervised training. In contrast, the conventional systems that include neural networks employ supervised training. The self-supervised training method described herein may also be applied to a conventional 3D tomography reconstruction system.

For the self-supervised training, simulated 2D tomography images are generated from the 3D density volumes output by a reconstruction pipeline, such as the 3D tomography reconstruction system 125. The 3D density volumes are projected, according to the capture environment that was used to generate the captured 2D tomography images, to produce simulated 2D tomography images. The simulated tomography images are each compared with the corresponding captured 2D tomography image (produced by a machine). The captured 2D tomography images that are input to the reconstruction pipeline are effectively used as reference (ground truth) 2D tomography images.

A loss function may be computed based on differences between the simulated 2D tomography images and the captured 2D tomography images. Differences determined by the loss function are backpropagated to update the neural network model parameters of the reconstruction pipeline. Even when the captured 2D tomography images are noisy and/or corrupted, the reconstruction pipeline learns to generate noise free reconstructions. The ability of the reconstruction pipeline to learn to generate noise free 3D density volumes may seem surprising and is explained by noise-to-noise principles described by Lehtinen et al. in "Noise2Noise: Learning Image Restoration without Clean Data," International Conference on Machine Learning (ICML) October 2018. The noise in the tomography images is zero-mean photon noise and the expected difference is minimized for the optimal 3D density volume. In sum, the reconstruction pipeline can learn to remove noise from images—even when trained using only noisy input images. Therefore, the reconstruction pipeline can learn to generate 3D density volumes with little or no noise—even when trained using only noisy tomography images.

Figure 3A:
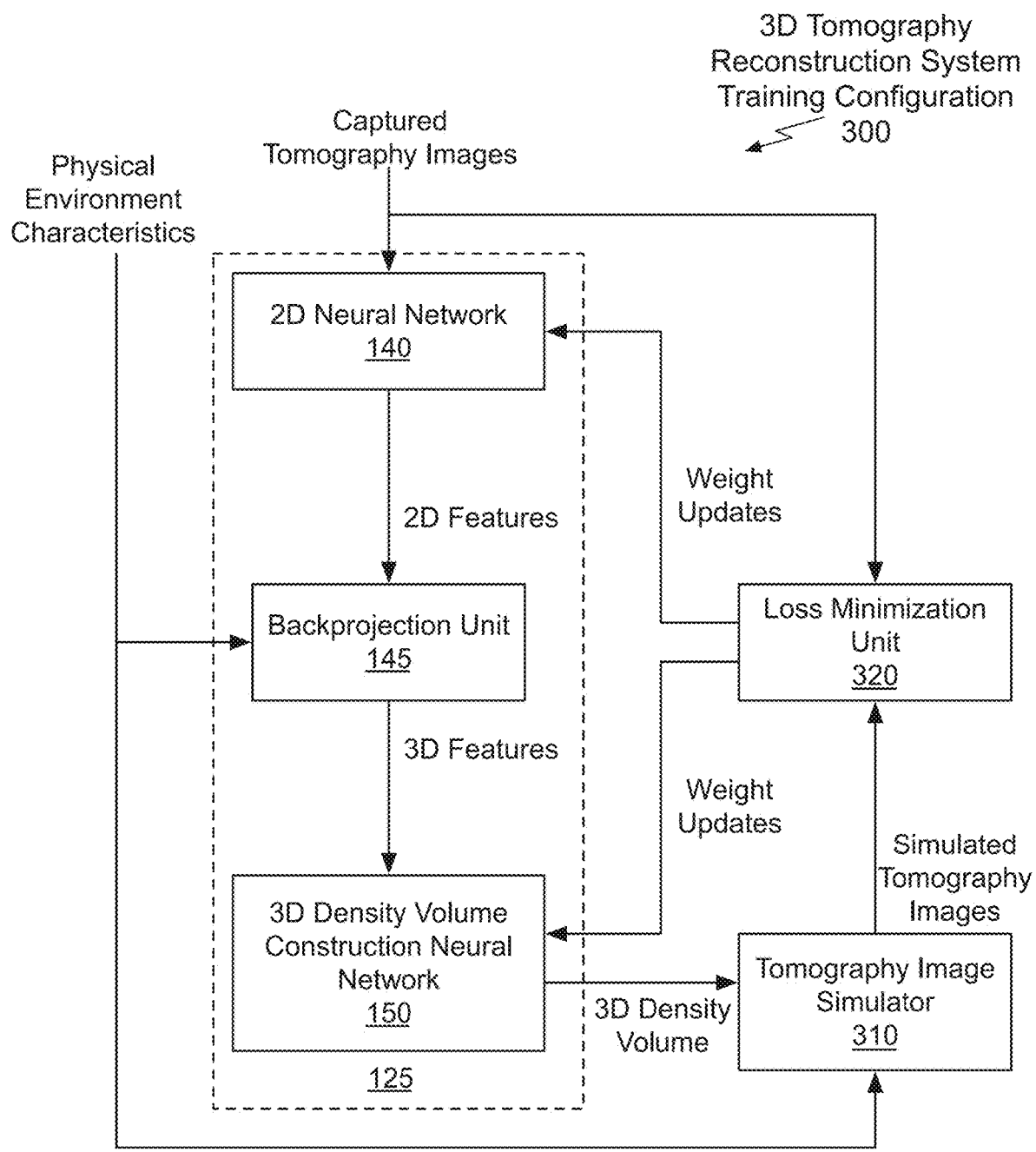
FIG. 3A illustrates a block diagram of an example 3D tomography reconstruction system training configuration suitable for use in implementing some embodiments of the present disclosure.

FIG. 3A illustrates a block diagram of an example 3D tomography reconstruction system training configuration 300 suitable for use in implementing some embodiments of the present disclosure. It should be understood that this and other arrangements described herein are set forth only as examples. Other arrangements and elements (e.g., machines, interfaces, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory. Furthermore, persons of ordinary skill in the art will understand that any system that performs the operations of the 3D tomography reconstruction system training configuration 300 is within the scope and spirit of embodiments of the present disclosure.

The 3D tomography reconstruction system training configuration 300 includes the 3D tomography reconstruction system 125, a tomography image simulator 310, and a loss minimization unit 320. The tomography image simulator 310 receives the 3D density volume and generates simulated tomography images corresponding to the captured tomography images. In an embodiment, the tomography image simulator 310 performs ray marching operations to generate the simulated tomography images. The tomography image simulator 310 simulates what the reconstructed 3D density volume would produce, when imaged in the capture environment. If the 3D density volume is an accurate representation of the physical volume being imaged, the simulated tomography images should be similar to the captured tomography images. In an embodiment, the simulated tomography images match the captured tomography images without noise.

The loss minimization unit 320 identifies differences between the simulated tomography images and the (captured) tomography images to generate a training signal for updating parameters of the 2D neural network 140 and the 3D density volume construction neural network 150. In an embodiment, the loss minimization unit 320 generates weight updates to minimize the differences using L2 norm (least-square error). In an embodiment, self-supervised training is performed using as many tomography images as are available. In an embodiment, the number of input tomography images is limited to, e.g., introduce randomness in the training, improve robustness to different physical setups, or enable evaluating the system with a distinct validation set. The tomography images need not be associated with the same object. Therefore, training datasets of captured tomography images are easily acquired. The training dataset may include tomography images having a high level of noise that are captured using low radiation doses and/or tomography images having a lower level of noise that are captured using higher radiation doses. In an embodiment, a different subset of the tomography images is used in each training iteration.

Figure 3B:
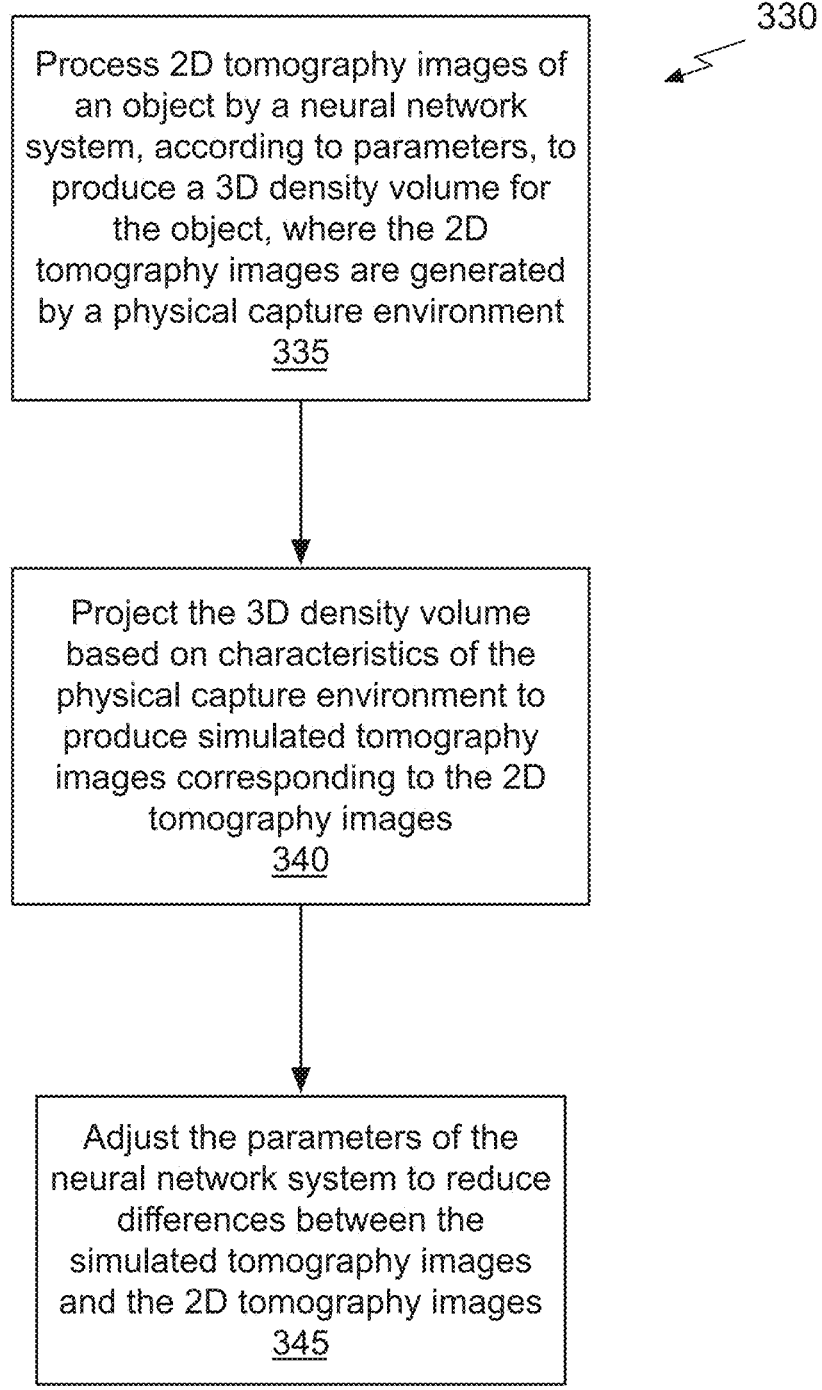
FIG. 3B illustrates a flowchart of a method for training a 3D tomography reconstruction system suitable for use in implementing some embodiments of the present disclosure.

FIG. 3B illustrates a flowchart of a method 330 for training a 3D tomography reconstruction system suitable for use in implementing some embodiments of the present disclosure. Each block of method 330, described herein, comprises a computing process that may be performed using any combination of hardware, firmware, and/or software. For instance, various functions may be carried out by a processor executing instructions stored in memory. The method may also be embodied as computer-usable instructions stored on computer storage media. The method may be provided by a standalone application, a service or hosted service (standalone or in combination with another hosted service), or a plug-in to another product, to name a few. In addition, method 330 is described, by way of example, with respect to the systems of FIGS. 1B and 3A. However, this method may additionally or alternatively be executed by any one system, or any combination of systems, including, but not limited to, those described herein. Furthermore, persons of ordinary skill in the art will understand that any system that performs method 330 is within the scope and spirit of embodiments of the present disclosure.

At step 335, 2D tomography images of an object are processed by a neural network system, according to parameters, to produce a 3D density volume for the object. In an embodiment, the 2D tomography images are generated by a physical capture environment. In an embodiment, the neural network system is the 3D tomography reconstruction system 125. In an embodiment, the entire 3D density volume is reconstructed. In an embodiment, the neural network system produces a set of slices of a 3D volume for the object instead of the entire 3D density volume. In an embodiment, the 3D density volume corresponds to a portion of a human body. In an embodiment, the physical capture environment comprises a conical spiral computerized tomography machine.

In an embodiment, the neural network system computes 3D data by backprojecting the 2D tomography images according to characteristics of the physical capture environment and processing the 3D data by a neural network model to produce the 3D density volume. In an embodiment, the backprojecting includes computing a projected footprint for a pixel and accessing one or more pre-filtered versions of the 2D tomography images according to at least one dimension of the projected footprint.

In an embodiment, the neural network system produces the 3D density volume by: processing the 2D tomography images by a first neural network model to produce at least one channel of 2D features; computing three-dimensional features by backprojecting the at least one channel of 2D features according to the characteristics; and processing the 3D features by a second neural network to produce the 3D density volume corresponding to the 2D tomography images. In an embodiment, the backprojecting includes computing a projected footprint for a pixel and accessing one or more pre-filtered versions of the at least one channel of 2D features according to at least one dimension of the projected footprint.

At step 340, the 3D density volume is projected based on characteristics of the physical capture environment to produce simulated tomography images corresponding to the 2D tomography images. In an embodiment, noise present in the 2D tomography images is reduced in the simulated tomography images. The projection operation may implement ray marching to integrate the 3D density volume along the rays that correspond to pixels of the tomography images, i.e., a discretized version of the standard volume attenuation line integral which describes how tomography images relate to the underlying 3D density volume. Formulas for the projection operation are detailed as formulas 2.1 and 2.2 in H. Turbell, "Cone-beam reconstruction using filtered backprojection" Ph.D. thesis, University of Linköping, Sweden, February 2001.

At step 345, the parameters of the neural network system are adjusted to reduce differences between the simulated tomography images and the 2D tomography images. In an embodiment, the parameters are weights of the 2D neural network 140 and/or the 3D density volume construction neural network 150. In an embodiment, steps 335, 340, and 345 are repeated for additional 2D tomography images of an additional object. In an embodiment, steps 335, 340, and 345 are repeated several times for one or more objects. In an embodiment, only a subset of the available 2D tomography images is used at a time.

Self-supervised training of a neural network-based tomography reconstruction system may be used without ground truth reference data. Instead of requiring reference 3D density data, as is used for supervised training, simulated tomography images are generated from 3D density data (e.g., the entire 3D density volume or a set of slices). The simulated tomography images are generated during self-supervised training using the 3D density data output by the neural network-based tomography reconstruction system. Simulated tomography images may be advantageously generated that correspond with all of the available 2D tomography images for a particular subject.

Parallel Processing Architecture

Figure 4:
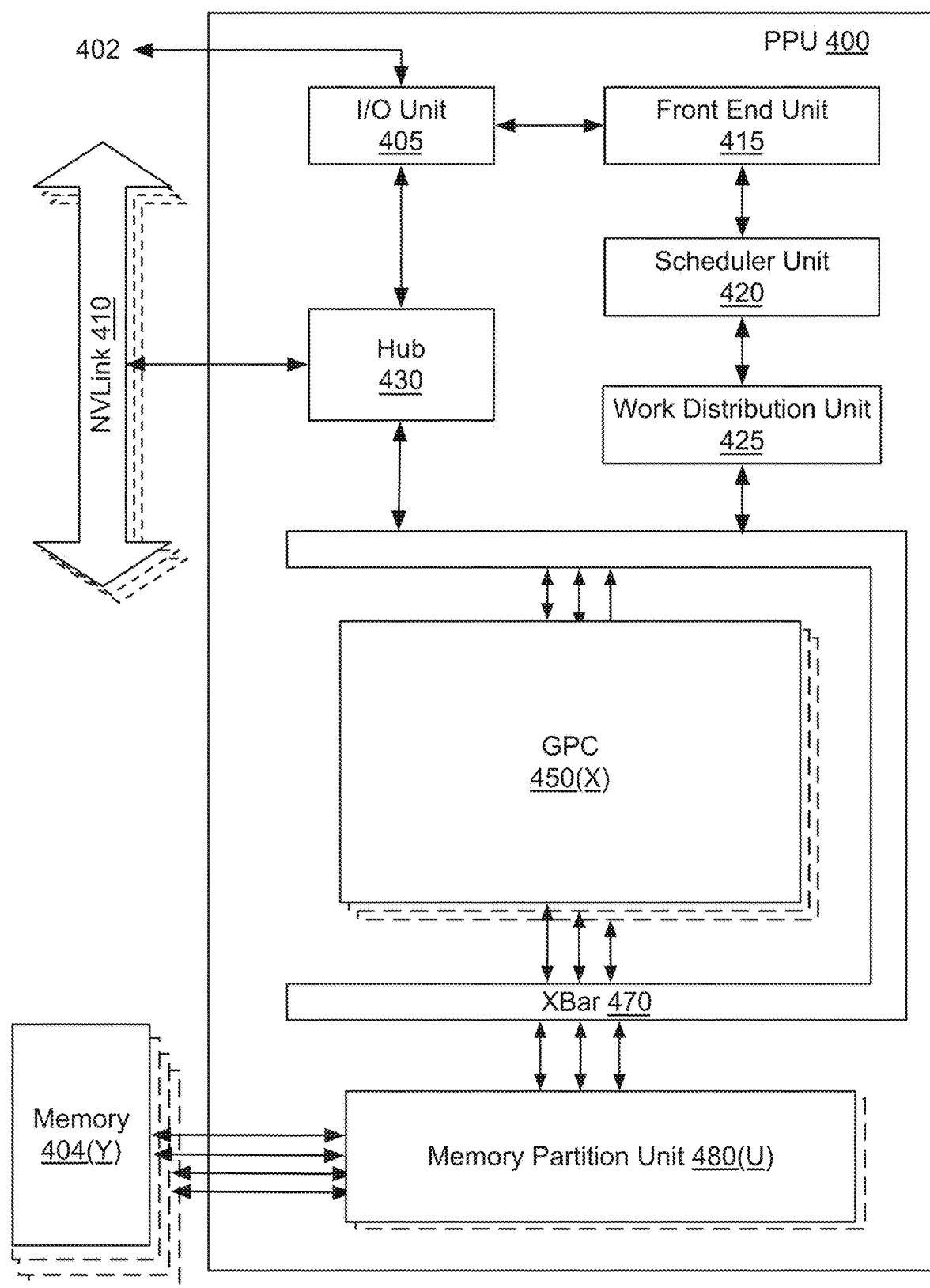
FIG. 4 illustrates an example parallel processing unit suitable for use in implementing some embodiments of the present disclosure.

FIG. 4 illustrates a parallel processing unit (PPU) 400, in accordance with an embodiment. The PPU 400 may be used to implement the 3D tomography reconstruction system 125 and/or the 3D tomography reconstruction system training configuration 300. The PPU 400 may be used to implement one or more of the 2D neural network 140, backprojection unit 145, 3D density volume construction neural network 150, slice generation unit 185, tomography image simulator 310, and loss minimization unit 320. In an embodiment, a processor such as the PPU 400 may be configured to implement a neural network model. The neural network model may be implemented as software instructions executed by the processor or, in other embodiments, the processor can include a matrix of hardware elements configured to process a set of inputs (e.g., electrical signals representing values) to generate a set of outputs, which can represent activations of the neural network model. In yet other embodiments, the neural network model can be implemented as a combination of software instructions and processing performed by a matrix of hardware elements. Implementing the neural network model can include determining a set of parameters for the neural network model through, e.g., supervised or unsupervised training of the neural network model as well as, or in the alternative, performing inference using the set of parameters to process novel sets of inputs.

In an embodiment, the PPU 400 is a multi-threaded processor that is implemented on one or more integrated circuit devices. The PPU 400 is a latency hiding architecture designed to process many threads in parallel. A thread (e.g., a thread of execution) is an instantiation of a set of instructions configured to be executed by the PPU 400. In an embodiment, the PPU 400 is a graphics processing unit (GPU) configured to implement a graphics rendering pipeline for processing three-dimensional (3D) graphics data in order to generate two-dimensional (2D) image data for display on a display device. In other embodiments, the PPU 400 may be utilized for performing general-purpose computations. While one exemplary parallel processor is provided herein for illustrative purposes, it should be strongly noted that such processor is set forth for illustrative purposes only, and that any processor may be employed to supplement and/or substitute for the same.

One or more PPUs 400 may be configured to accelerate thousands of High Performance Computing (HPC), data center, cloud computing, and machine learning applications. The PPU 400 may be configured to accelerate numerous deep learning systems and applications for autonomous vehicles, simulation, computational graphics such as ray or path tracing, deep learning, high-accuracy speech, image, and text recognition systems, intelligent video analytics, molecular simulations, drug discovery, disease diagnosis, weather forecasting, big data analytics, astronomy, molecular dynamics simulation, financial modeling, robotics, factory automation, real-time language translation, online search optimizations, and personalized user recommendations, and the like.

As shown in FIG. 4, the PPU 400 includes an Input/Output (I/O) unit 405, a front end unit 415, a scheduler unit 420, a work distribution unit 425, a hub 430, a crossbar (Xbar) 470, one or more general processing clusters (GPCs) 450, and one or more memory partition units 480. The PPU 400 may be connected to a host processor or other PPUs 400 via one or more high-speed NVLink 410 interconnect. The PPU 400 may be connected to a host processor or other peripheral devices via an interconnect 402. The PPU 400 may also be connected to a local memory 404 comprising a number of memory devices. In an embodiment, the local memory may comprise a number of dynamic random access memory (DRAM) devices. The DRAM devices may be configured as a high-bandwidth memory (HBM) subsystem, with multiple DRAM dies stacked within each device.

The NVLink 410 interconnect enables systems to scale and include one or more PPUs 400 combined with one or more CPUs, supports cache coherence between the PPUs 400 and CPUs, and CPU mastering. Data and/or commands may be transmitted by the NVLink 410 through the hub 430 to/from other units of the PPU 400 such as one or more copy engines, a video encoder, a video decoder, a power management unit, etc. (not explicitly shown). The NVLink 410 is described in more detail in conjunction with FIG. 5B.

The I/O unit 405 is configured to transmit and receive communications (e.g., commands, data, etc.) from a host processor (not shown) over the interconnect 402. The I/O unit 405 may communicate with the host processor directly via the interconnect 402 or through one or more intermediate devices such as a memory bridge. In an embodiment, the I/O unit 405 may communicate with one or more other processors, such as one or more the PPUs 400 via the interconnect 402. In an embodiment, the I/O unit 405 implements a Peripheral Component Interconnect Express (PCIe) interface for communications over a PCIe bus and the interconnect 402 is a PCIe bus. In alternative embodiments, the I/O unit 405 may implement other types of well-known interfaces for communicating with external devices.

The I/O unit 405 decodes packets received via the interconnect 402. In an embodiment, the packets represent commands configured to cause the PPU 400 to perform various operations. The I/O unit 405 transmits the decoded commands to various other units of the PPU 400 as the commands may specify. For example, some commands may be transmitted to the front end unit 415. Other commands may be transmitted to the hub 430 or other units of the PPU 400 such as one or more copy engines, a video encoder, a video decoder, a power management unit, etc. (not explicitly shown). In other words, the I/O unit 405 is configured to route communications between and among the various logical units of the PPU 400.

In an embodiment, a program executed by the host processor encodes a command stream in a buffer that provides workloads to the PPU 400 for processing. A workload may comprise several instructions and data to be processed by those instructions. The buffer is a region in a memory that is accessible (e.g., read/write) by both the host processor and the PPU 400. For example, the I/O unit 405 may be configured to access the buffer in a system memory connected to the interconnect 402 via memory requests transmitted over the interconnect 402. In an embodiment, the host processor writes the command stream to the buffer and then transmits a pointer to the start of the command stream to the PPU 400. The front end unit 415 receives pointers to one or more command streams. The front end unit 415 manages the one or more streams, reading commands from the streams and forwarding commands to the various units of the PPU 400.

The front end unit 415 is coupled to a scheduler unit 420 that configures the various GPCs 450 to process tasks defined by the one or more streams. The scheduler unit 420 is configured to track state information related to the various tasks managed by the scheduler unit 420. The state may indicate which GPC 450 a task is assigned to, whether the task is active or inactive, a priority level associated with the task, and so forth. The scheduler unit 420 manages the execution of a plurality of tasks on the one or more GPCs 450.

The scheduler unit 420 is coupled to a work distribution unit 425 that is configured to dispatch tasks for execution on the GPCs 450. The work distribution unit 425 may track a number of scheduled tasks received from the scheduler unit 420. In an embodiment, the work distribution unit 425 manages a pending task pool and an active task pool for each of the GPCs 450. As a GPC 450 finishes the execution of a task, that task is evicted from the active task pool for the GPC 450 and one of the other tasks from the pending task pool is selected and scheduled for execution on the GPC 450. If an active task has been idle on the GPC 450, such as while waiting for a data dependency to be resolved, then the active task may be evicted from the GPC 450 and returned to the pending task pool while another task in the pending task pool is selected and scheduled for execution on the GPC 450.

In an embodiment, a host processor executes a driver kernel that implements an application programming interface (API) that enables one or more applications executing on the host processor to schedule operations for execution on the PPU 400. In an embodiment, multiple compute applications are simultaneously executed by the PPU 400 and the PPU 400 provides isolation, quality of service (QoS), and independent address spaces for the multiple compute applications. An application may generate instructions (e.g., API calls) that cause the driver kernel to generate one or more tasks for execution by the PPU 400. The driver kernel outputs tasks to one or more streams being processed by the PPU 400. Each task may comprise one or more groups of related threads, referred to herein as a warp. In an embodiment, a warp comprises 32 related threads that may be executed in parallel. Cooperating threads may refer to a plurality of threads including instructions to perform the task and that may exchange data through shared memory. The tasks may be allocated to one or more processing units within a GPC 450 and instructions are scheduled for execution by at least one warp.

The work distribution unit 425 communicates with the one or more GPCs 450 via XBar 470. The XBar 470 is an interconnect network that couples many of the units of the PPU 400 to other units of the PPU 400. For example, the XBar 470 may be configured to couple the work distribution unit 425 to a particular GPC 450. Although not shown explicitly, one or more other units of the PPU 400 may also be connected to the XBar 470 via the hub 430.

The tasks are managed by the scheduler unit 420 and dispatched to a GPC 450 by the work distribution unit 425. The GPC 450 is configured to process the task and generate results. The results may be consumed by other tasks within the GPC 450, routed to a different GPC 450 via the XBar 470, or stored in the memory 404. The results can be written to the memory 404 via the memory partition units 480, which implement a memory interface for reading and writing data to/from the memory 404. The results can be transmitted to another PPU 400 or CPU via the NVLink 410. In an embodiment, the PPU 400 includes a number U of memory partition units 480 that is equal to the number of separate and distinct memory devices of the memory 404 coupled to the PPU 400. Each GPC 450 may include a memory management unit to provide translation of virtual addresses into physical addresses, memory protection, and arbitration of memory requests. In an embodiment, the memory management unit provides one or more translation lookaside buffers (TLBs) for performing translation of virtual addresses into physical addresses in the memory 404.

In an embodiment, the memory partition unit 480 includes a Raster Operations (ROP) unit, a level two (L2) cache, and a memory interface that is coupled to the memory 404. The memory interface may implement 32, 64, 128, 1024-bit data buses, or the like, for high-speed data transfer. The PPU 400 may be connected to up to Y memory devices, such as high bandwidth memory stacks or graphics double-data-rate, version 5, synchronous dynamic random access memory, or other types of persistent storage. In an embodiment, the memory interface implements an HBM2 memory interface and Y equals half U. In an embodiment, the HBM2 memory stacks are located on the same physical package as the PPU 400, providing substantial power and area savings compared with conventional GDDR5 SDRAM systems. In an embodiment, each HBM2 stack includes four memory dies and Y equals 4, with each HBM2 stack including two 128-bit channels per die for a total of 8 channels and a data bus width of 1024 bits.

In an embodiment, the memory 404 supports Single-Error Correcting Double-Error Detecting (SECDED) Error Correction Code (ECC) to protect data. ECC provides higher reliability for compute applications that are sensitive to data corruption. Reliability is especially important in large-scale cluster computing environments where PPUs 400 process very large datasets and/or run applications for extended periods.

In an embodiment, the PPU 400 implements a multi-level memory hierarchy. In an embodiment, the memory partition unit 480 supports a unified memory to provide a single unified virtual address space for CPU and PPU 400 memory, enabling data sharing between virtual memory systems. In an embodiment the frequency of accesses by a PPU 400 to memory located on other processors is traced to ensure that memory pages are moved to the physical memory of the PPU 400 that is accessing the pages more frequently. In an embodiment, the NVLink 410 supports address translation services allowing the PPU 400 to directly access a CPU's page tables and providing full access to CPU memory by the PPU 400.

In an embodiment, copy engines transfer data between multiple PPUs 400 or between PPUs 400 and CPUs. The copy engines can generate page faults for addresses that are not mapped into the page tables. The memory partition unit 480 can then service the page faults, mapping the addresses into the page table, after which the copy engine can perform the transfer. In a conventional system, memory is pinned (e.g., non-pageable) for multiple copy engine operations between multiple processors, substantially reducing the available memory. With hardware page faulting, addresses can be passed to the copy engines without worrying if the memory pages are resident, and the copy process is transparent.

Data from the memory 404 or other system memory may be fetched by the memory partition unit 480 and stored in the L2 cache 460, which is located on-chip and is shared between the various GPCs 450. As shown, each memory partition unit 480 includes a portion of the L2 cache associated with a corresponding memory 404. Lower level caches may then be implemented in various units within the GPCs 450. For example, each of the processing units within a GPC 450 may implement a level one (L1) cache. The L1 cache is private memory that is dedicated to a particular processing unit. The L2 cache 460 is coupled to the memory interface 470 and the XBar 470 and data from the L2 cache may be fetched and stored in each of the L1 caches for processing.

In an embodiment, the processing units within each GPC 450 implement a SIMD (Single-Instruction, Multiple-Data) architecture where each thread in a group of threads (e.g., a warp) is configured to process a different set of data based on the same set of instructions. All threads in the group of threads execute the same instructions. In another embodiment, the processing unit implements a SIMT (Single-Instruction, Multiple Thread) architecture where each thread in a group of threads is configured to process a different set of data based on the same set of instructions, but where individual threads in the group of threads are allowed to diverge during execution. In an embodiment, a program counter, call stack, and execution state is maintained for each warp, enabling concurrency between warps and serial execution within warps when threads within the warp diverge. In another embodiment, a program counter, call stack, and execution state is maintained for each individual thread, enabling equal concurrency between all threads, within and between warps. When execution state is maintained for each individual thread, threads executing the same instructions may be converged and executed in parallel for maximum efficiency.

Cooperative Groups is a programming model for organizing groups of communicating threads that allows developers to express the granularity at which threads are communicating, enabling the expression of richer, more efficient parallel decompositions. Cooperative launch APIs support synchronization amongst thread blocks for the execution of parallel algorithms. Conventional programming models provide a single, simple construct for synchronizing cooperating threads: a barrier across all threads of a thread block (e.g., the syncthreads( ) function). However, programmers would often like to define groups of threads at smaller than thread block granularities and synchronize within the defined groups to enable greater performance, design flexibility, and software reuse in the form of collective group-wide function interfaces.

Cooperative Groups enables programmers to define groups of threads explicitly at sub-block (e.g., as small as a single thread) and multi-block granularities, and to perform collective operations such as synchronization on the threads in a cooperative group. The programming model supports clean composition across software boundaries, so that libraries and utility functions can synchronize safely within their local context without having to make assumptions about convergence. Cooperative Groups primitives enable new patterns of cooperative parallelism, including producer-consumer parallelism, opportunistic parallelism, and global synchronization across an entire grid of thread blocks.

Each processing unit includes a large number (e.g., 128, etc.) of distinct processing cores (e.g., functional units) that may be fully-pipelined, single-precision, double-precision, and/or mixed precision and include a floating point arithmetic logic unit and an integer arithmetic logic unit. In an embodiment, the floating point arithmetic logic units implement the IEEE 754-2008 standard for floating point arithmetic. In an embodiment, the cores include 64 single-precision (32-bit) floating point cores, 64 integer cores, 32 double-precision (64-bit) floating point cores, and 8 tensor cores.

Tensor cores configured to perform matrix operations. In particular, the tensor cores are configured to perform deep learning matrix arithmetic, such as GEMM (matrix-matrix multiplication) for convolution operations during neural network training and inferencing. In an embodiment, each tensor core operates on a 4×4 matrix and performs a matrix multiply and accumulate operation D=A×B+C, where A, B, C, and D are 4×4 matrices.

In an embodiment, the matrix multiply inputs A and B may be integer, fixed-point, or floating point matrices, while the accumulation matrices C and D may be integer, fixed-point, or floating point matrices of equal or higher bitwidths. In an embodiment, tensor cores operate on one, four, or eight bit integer input data with 32-bit integer accumulation. The 8-bit integer matrix multiply requires 1024 operations and results in a full precision product that is then accumulated using 32-bit integer addition with the other intermediate products for a 8×8×16 matrix multiply. In an embodiment, tensor Cores operate on 16-bit floating point input data with 32-bit floating point accumulation. The 16-bit floating point multiply requires 64 operations and results in a full precision product that is then accumulated using 32-bit floating point addition with the other intermediate products for a 4×4×4 matrix multiply. In practice, Tensor Cores are used to perform much larger two-dimensional or higher dimensional matrix operations, built up from these smaller elements. An API, such as CUDA 9 C++ API, exposes specialized matrix load, matrix multiply and accumulate, and matrix store operations to efficiently use Tensor Cores from a CUDA-C++ program. At the CUDA level, the warp-level interface assumes 16×16 size matrices spanning all 32 threads of the warp.

Each processing unit may also comprise M special function units (SFUs) that perform special functions (e.g., attribute evaluation, reciprocal square root, and the like). In an embodiment, the SFUs may include a tree traversal unit configured to traverse a hierarchical tree data structure. In an embodiment, the SFUs may include texture unit configured to perform texture map filtering operations. In an embodiment, the texture units are configured to load texture maps (e.g., a 2D array of texels) from the memory 404 and sample the texture maps to produce sampled texture values for use in shader programs executed by the processing unit. In an embodiment, the texture maps are stored in shared memory that may comprise or include an L1 cache. The texture units implement texture operations such as filtering operations using mip-maps (e.g., texture maps of varying levels of detail). In an embodiment, each processing unit includes two texture units.

Each processing unit also comprises N load store units (LSUs) that implement load and store operations between the shared memory and the register file. Each processing unit includes an interconnect network that connects each of the cores to the register file and the LSU to the register file, shared memory. In an embodiment, the interconnect network is a crossbar that can be configured to connect any of the cores to any of the registers in the register file and connect the LSUs to the register file and memory locations in shared memory.

The shared memory is an array of on-chip memory that allows for data storage and communication between the processing units and between threads within a processing unit. In an embodiment, the shared memory comprises 128 KB of storage capacity and is in the path from each of the processing units to the memory partition unit 480. The shared memory can be used to cache reads and writes. One or more of the shared memory, L1 cache, L2 cache, and memory 404 are backing stores.

Combining data cache and shared memory functionality into a single memory block provides the best overall performance for both types of memory accesses. The capacity is usable as a cache by programs that do not use shared memory. For example, if shared memory is configured to use half of the capacity, texture and load/store operations can use the remaining capacity. Integration within the shared memory enables the shared memory to function as a high-throughput conduit for streaming data while simultaneously providing high-bandwidth and low-latency access to frequently reused data.

When configured for general purpose parallel computation, a simpler configuration can be used compared with graphics processing. Specifically, fixed function graphics processing units, are bypassed, creating a much simpler programming model. In the general purpose parallel computation configuration, the work distribution unit 425 assigns and distributes blocks of threads directly to the processing units within the GPCs 450. Threads execute the same program, using a unique thread ID in the calculation to ensure each thread generates unique results, using the processing unit(s) to execute the program and perform calculations, shared memory to communicate between threads, and the LSU to read and write global memory through the shared memory and the memory partition unit 480. When configured for general purpose parallel computation, the processing units can also write commands that the scheduler unit 420 can use to launch new work on the processing units.

The PPUs 400 may each include, and/or be configured to perform functions of, one or more processing cores and/or components thereof, such as Tensor Cores (TCs), Tensor Processing Units (TPUs), Pixel Visual Cores (PVCs), Ray Tracing (RT) Cores, Vision Processing Units (VPUs), Graphics Processing Clusters (GPCs), Texture Processing Clusters (TPCs), Streaming Multiprocessors (SMs), Tree Traversal Units (TTUs), Artificial Intelligence Accelerators (AIAs), Deep Learning Accelerators (DLAs), Arithmetic-Logic Units (ALUs), Application-Specific Integrated Circuits (ASICs), Floating Point Units (FPUs), input/output (I/O) elements, peripheral component interconnect (PCI) or peripheral component interconnect express (PCIe) elements, and/or the like.

The PPU 400 may be included in a desktop computer, a laptop computer, a tablet computer, servers, supercomputers, a smart-phone (e.g., a wireless, hand-held device), personal digital assistant (PDA), a digital camera, a vehicle, a head mounted display, a hand-held electronic device, and the like. In an embodiment, the PPU 400 is embodied on a single semiconductor substrate. In another embodiment, the PPU 400 is included in a system-on-a-chip (SoC) along with one or more other devices such as additional PPUs 400, the memory 404, a reduced instruction set computer (RISC) CPU, a memory management unit (MMU), a digital-to-analog converter (DAC), and the like.

In an embodiment, the PPU 400 may be included on a graphics card that includes one or more memory devices. The graphics card may be configured to interface with a PCIe slot on a motherboard of a desktop computer. In yet another embodiment, the PPU 400 may be an integrated graphics processing unit (iGPU) or parallel processor included in the chipset of the motherboard. In yet another embodiment, the PPU 400 may be realized in reconfigurable hardware. In yet another embodiment, parts of the PPU 400 may be realized in reconfigurable hardware.

Exemplary Computing System

Systems with multiple GPUs and CPUs are used in a variety of industries as developers expose and leverage more parallelism in applications such as artificial intelligence computing. High-performance GPU-accelerated systems with tens to many thousands of compute nodes are deployed in data centers, research facilities, and supercomputers to solve ever larger problems. As the number of processing devices within the high-performance systems increases, the communication and data transfer mechanisms need to scale to support the increased bandwidth.

Figure 5A:
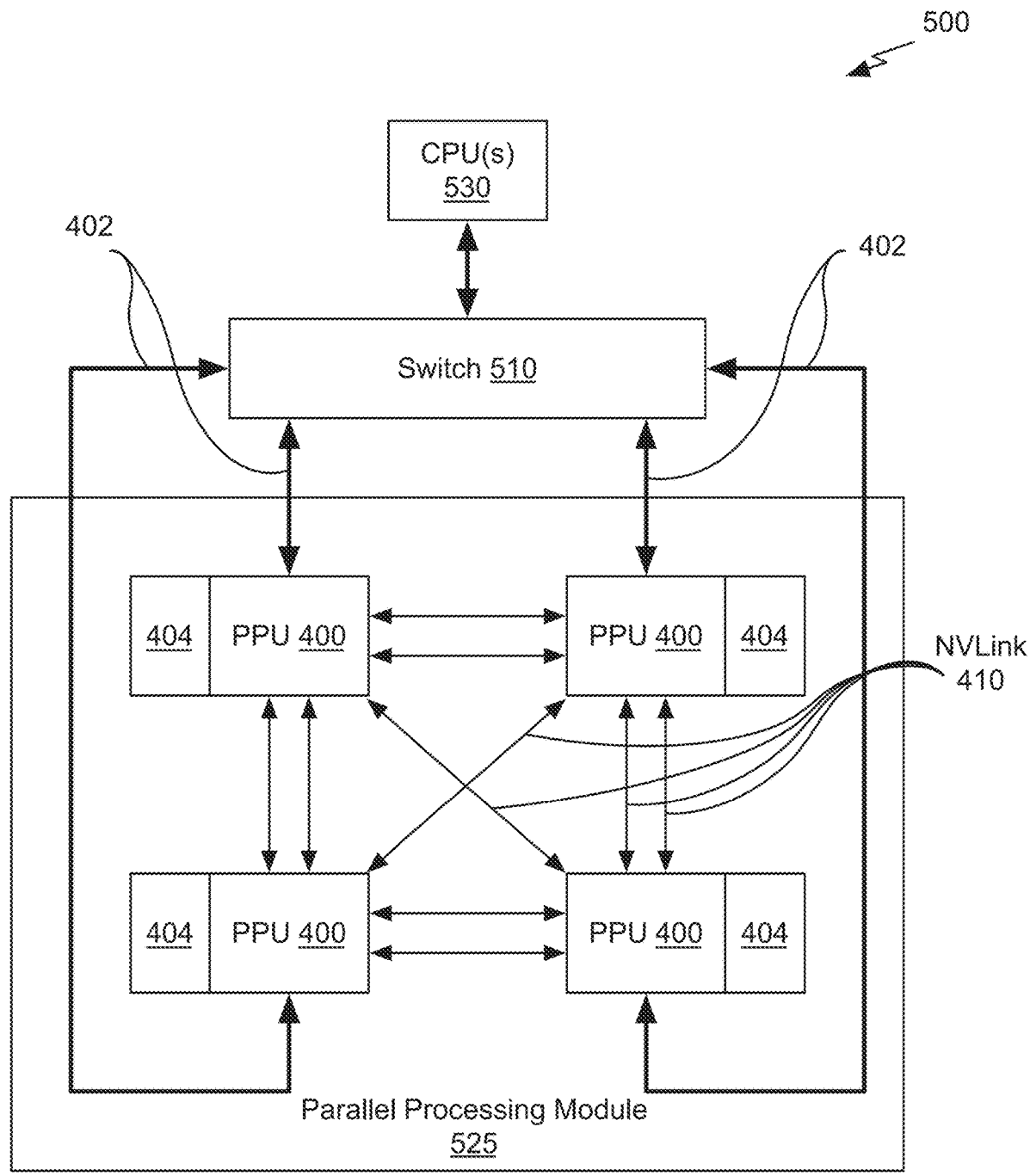
FIG. 5A is a conceptual diagram of a processing system implemented using the PPU of FIG. 4, suitable for use in implementing some embodiments of the present disclosure.

FIG. 5A is a conceptual diagram of a processing system 500 implemented using the PPU 400 of FIG. 4, in accordance with an embodiment. The exemplary system 500 may be configured to implement the method 160 shown in FIG. 1C and/or the method 330 shown in FIG. 3B. The processing system 500 includes a CPU 530, switch 510, and multiple PPUs 400, and respective memories 404.

Figure 5B:
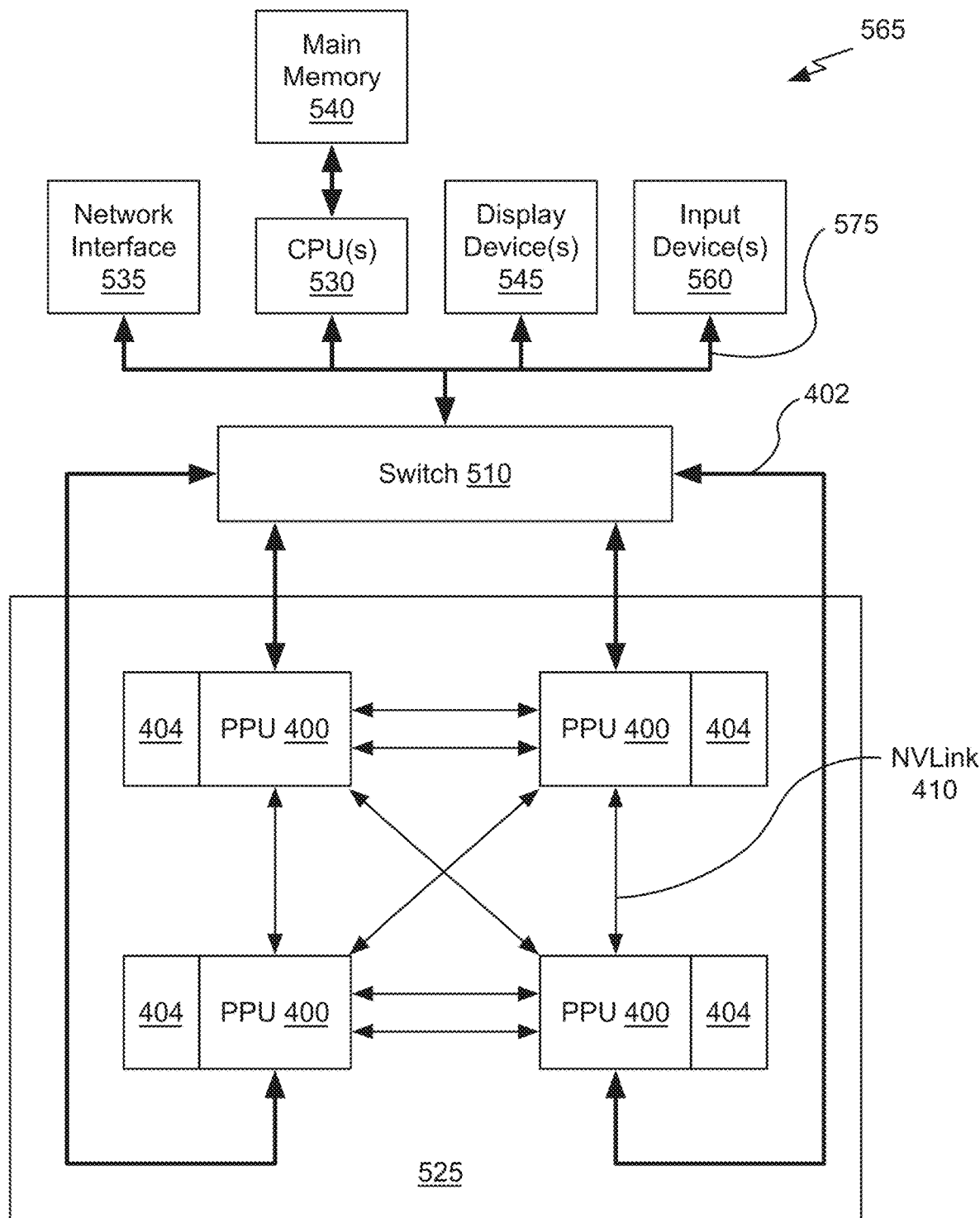
FIG. 5B illustrates an exemplary system in which the various architecture and/or functionality of the various previous embodiments may be implemented.

The NVLink 410 provides high-speed communication links between each of the PPUs 400. Although a particular number of NVLink 410 and interconnect 402 connections are illustrated in FIG. 5B, the number of connections to each PPU 400 and the CPU 530 may vary. The switch 510 interfaces between the interconnect 402 and the CPU 530. The PPUs 400, memories 404, and NVLinks 410 may be situated on a single semiconductor platform to form a parallel processing module 525. In an embodiment, the switch 510 supports two or more protocols to interface between various different connections and/or links.

In another embodiment (not shown), the NVLink 410 provides one or more high-speed communication links between each of the PPUs 400 and the CPU 530 and the switch 510 interfaces between the interconnect 402 and each of the PPUs 400. The PPUs 400, memories 404, and interconnect 402 may be situated on a single semiconductor platform to form a parallel processing module 525. In yet another embodiment (not shown), the interconnect 402 provides one or more communication links between each of the PPUs 400 and the CPU 530 and the switch 510 interfaces between each of the PPUs 400 using the NVLink 410 to provide one or more high-speed communication links between the PPUs 400. In another embodiment (not shown), the NVLink 410 provides one or more high-speed communication links between the PPUs 400 and the CPU 530 through the switch 510. In yet another embodiment (not shown), the interconnect 402 provides one or more communication links between each of the PPUs 400 directly. One or more of the NVLink 410 high-speed communication links may be implemented as a physical NVLink interconnect or either an on-chip or on-die interconnect using the same protocol as the NVLink 410.

In the context of the present description, a single semiconductor platform may refer to a sole unitary semiconductor-based integrated circuit fabricated on a die or chip. It should be noted that the term single semiconductor platform may also refer to multi-chip modules with increased connectivity which simulate on-chip operation and make substantial improvements over utilizing a conventional bus implementation. Of course, the various circuits or devices may also be situated separately or in various combinations of semiconductor platforms per the desires of the user. Alternately, the parallel processing module 525 may be implemented as a circuit board substrate and each of the PPUs 400 and/or memories 404 may be packaged devices. In an embodiment, the CPU 530, switch 510, and the parallel processing module 525 are situated on a single semiconductor platform.

In an embodiment, the signaling rate of each NVLink 410 is 20 to 25 Gigabits/second and each PPU 400 includes six NVLink 410 interfaces (as shown in FIG. 5A, five NVLink 410 interfaces are included for each PPU 400). Each NVLink 410 provides a data transfer rate of 25 Gigabytes/second in each direction, with six links providing 400 Gigabytes/second. The NVLinks 410 can be used exclusively for PPU-to-PPU communication as shown in FIG. 5A, or some combination of PPU-to-PPU and PPU-to-CPU, when the CPU 530 also includes one or more NVLink 410 interfaces.

In an embodiment, the NVLink 410 allows direct load/store/atomic access from the CPU 530 to each PPU's 400 memory 404. In an embodiment, the NVLink 410 supports coherency operations, allowing data read from the memories 404 to be stored in the cache hierarchy of the CPU 530, reducing cache access latency for the CPU 530. In an embodiment, the NVLink 410 includes support for Address Translation Services (ATS), allowing the PPU 400 to directly access page tables within the CPU 530. One or more of the NVLinks 410 may also be configured to operate in a low-power mode.

FIG. 5B illustrates an exemplary system 565 in which the various architecture and/or functionality of the various previous embodiments may be implemented. The exemplary system 565 may be configured to implement the method 160 shown in FIG. 1C and/or the method 330 shown in FIG. 3B.

As shown, a system 565 is provided including at least one central processing unit 530 that is connected to a communication bus 575. The communication bus 575 may directly or indirectly couple one or more of the following devices: main memory 540, network interface 535, CPU(s) 530, display device(s) 545, input device(s) 560, switch 510, and parallel processing system 525. The communication bus 575 may be implemented using any suitable protocol and may represent one or more links or busses, such as an address bus, a data bus, a control bus, or a combination thereof. The communication bus 575 may include one or more bus or link types, such as an industry standard architecture (ISA) bus, an extended industry standard architecture (EISA) bus, a video electronics standards association (VESA) bus, a peripheral component interconnect (PCI) bus, a peripheral component interconnect express (PCIe) bus, HyperTransport, and/or another type of bus or link. In some embodiments, there are direct connections between components. As an example, the CPU(s) 530 may be directly connected to the main memory 540. Further, the CPU(s) 530 may be directly connected to the parallel processing system 525.

Where there is direct, or point-to-point connection between components, the communication bus 575 may include a PCIe link to carry out the connection. In these examples, a PCI bus need not be included in the system 565.

Although the various blocks of FIG. 5B are shown as connected via the communication bus 575 with lines, this is not intended to be limiting and is for clarity only. For example, in some embodiments, a presentation component, such as display device(s) 545, may be considered an I/O component, such as input device(s) 560 (e.g., if the display is a touch screen). As another example, the CPU(s) 530 and/or parallel processing system 525 may include memory (e.g., the main memory 540 may be representative of a storage device in addition to the parallel processing system 525, the CPUs 530, and/or other components). In other words, the computing device of FIG. 5B is merely illustrative. Distinction is not made between such categories as "workstation," "server," "laptop," "desktop," "tablet," "client device," "mobile device," "hand-held device," "game console," "electronic control unit (ECU)," "virtual reality system," and/or other device or system types, as all are contemplated within the scope of the computing device of FIG. 5B.

The system 565 also includes a main memory 540. Control logic (software) and data are stored in the main memory 540 which may take the form of a variety of computer-readable media. The computer-readable media may be any available media that may be accessed by the system 565. The computer-readable media may include both volatile and nonvolatile media, and removable and non-removable media. By way of example, and not limitation, the computer-readable media may comprise computer-storage media and communication media.

The computer-storage media may include both volatile and nonvolatile media and/or removable and non-removable media implemented in any method or technology for storage of information such as computer-readable instructions, data structures, program modules, and/or other data types. For example, the main memory 540 may store computer-readable instructions (e.g., that represent a program(s) and/or a program element(s), such as an operating system. Computer-storage media may include, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which may be used to store the desired information and which may be accessed by system 565. As used herein, computer storage media does not comprise signals per se.

The computer storage media may embody computer-readable instructions, data structures, program modules, and/or other data types in a modulated data signal such as a carrier wave or other transport mechanism and includes any information delivery media. The term "modulated data signal" may refer to a signal that has one or more of its characteristics set or changed in such a manner as to encode information in the signal. By way of example, and not limitation, the computer storage media may include wired media such as a wired network or direct-wired connection, and wireless media such as acoustic, RF, infrared and other wireless media. Combinations of any of the above should also be included within the scope of computer-readable media.

Computer programs, when executed, enable the system 565 to perform various functions. The CPU(s) 530 may be configured to execute at least some of the computer-readable instructions to control one or more components of the system 565 to perform one or more of the methods and/or processes described herein. The CPU(s) 530 may each include one or more cores (e.g., one, two, four, eight, twenty-eight, seventy-two, etc.) that are capable of handling a multitude of software threads simultaneously. The CPU(s) 530 may include any type of processor, and may include different types of processors depending on the type of system 565 implemented (e.g., processors with fewer cores for mobile devices and processors with more cores for servers). For example, depending on the type of system 565, the processor may be an Advanced RISC Machines (ARM) processor implemented using Reduced Instruction Set Computing (RISC) or an x86 processor implemented using Complex Instruction Set Computing (CISC). The system 565 may include one or more CPUs 530 in addition to one or more microprocessors or supplementary co-processors, such as math co-processors.

In addition to or alternatively from the CPU(s) 530, the parallel processing module 525 may be configured to execute at least some of the computer-readable instructions to control one or more components of the system 565 to perform one or more of the methods and/or processes described herein. The parallel processing module 525 may be used by the system 565 to render graphics (e.g., 3D graphics) or perform general purpose computations. For example, the parallel processing module 525 may be used for General-Purpose computing on GPUs (GPGPU). In embodiments, the CPU(s) 530 and/or the parallel processing module 525 may discretely or jointly perform any combination of the methods, processes and/or portions thereof.

The system 565 also includes input device(s) 560, the parallel processing system 525, and display device(s) 545. The display device(s) 545 may include a display (e.g., a monitor, a touch screen, a television screen, a heads-up-display (HUD), other display types, or a combination thereof), speakers, and/or other presentation components. The display device(s) 545 may receive data from other components (e.g., the parallel processing system 525, the CPU(s) 530, etc.), and output the data (e.g., as an image, video, sound, etc.).

The network interface 535 may enable the system 565 to be logically coupled to other devices including the input devices 560, the display device(s) 545, and/or other components, some of which may be built in to (e.g., integrated in) the system 565. Illustrative input devices 560 include a microphone, mouse, keyboard, joystick, game pad, game controller, satellite dish, scanner, printer, wireless device, etc. The input devices 560 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the system 565. The system 565 may be include depth cameras, such as stereoscopic camera systems, infrared camera systems, RGB camera systems, touchscreen technology, and combinations of these, for gesture detection and recognition. Additionally, the system 565 may include accelerometers or gyroscopes (e.g., as part of an inertia measurement unit (IMU)) that enable detection of motion. In some examples, the output of the accelerometers or gyroscopes may be used by the system 565 to render immersive augmented reality or virtual reality.

Further, the system 565 may be coupled to a network (e.g., a telecommunications network, local area network (LAN), wireless network, wide area network (WAN) such as the Internet, peer-to-peer network, cable network, or the like) through a network interface 535 for communication purposes. The system 565 may be included within a distributed network and/or cloud computing environment.

The network interface 535 may include one or more receivers, transmitters, and/or transceivers that enable the system 565 to communicate with other computing devices via an electronic communication network, included wired and/or wireless communications. The network interface 535 may include components and functionality to enable communication over any of a number of different networks, such as wireless networks (e.g., Wi-Fi, Z-Wave, Bluetooth, Bluetooth LE, ZigBee, etc.), wired networks (e.g., communicating over Ethernet or InfiniBand), low-power wide-area networks (e.g., LoRaWAN, SigFox, etc.), and/or the Internet.

The system 565 may also include a secondary storage (not shown). The secondary storage includes, for example, a hard disk drive and/or a removable storage drive, representing a floppy disk drive, a magnetic tape drive, a compact disk drive, digital versatile disk (DVD) drive, recording device, universal serial bus (USB) flash memory. The removable storage drive reads from and/or writes to a removable storage unit in a well-known manner. The system 565 may also include a hard-wired power supply, a battery power supply, or a combination thereof (not shown). The power supply may provide power to the system 565 to enable the components of the system 565 to operate.

Each of the foregoing modules and/or devices may even be situated on a single semiconductor platform to form the system 565. Alternately, the various modules may also be situated separately or in various combinations of semiconductor platforms per the desires of the user. While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

Example Network Environments

Network environments suitable for use in implementing embodiments of the disclosure may include one or more client devices, servers, network attached storage (NAS), other backend devices, and/or other device types. The client devices, servers, and/or other device types (e.g., each device) may be implemented on one or more instances of the processing system 500 of FIG. 5A and/or exemplary system 565 of FIG. 5B—e.g., each device may include similar components, features, and/or functionality of the processing system 500 and/or exemplary system 565.

Components of a network environment may communicate with each other via a network(s), which may be wired, wireless, or both. The network may include multiple networks, or a network of networks. By way of example, the network may include one or more Wide Area Networks (WANs), one or more Local Area Networks (LANs), one or more public networks such as the Internet and/or a public switched telephone network (PSTN), and/or one or more private networks. Where the network includes a wireless telecommunications network, components such as a base station, a communications tower, or even access points (as well as other components) may provide wireless connectivity.

Compatible network environments may include one or more peer-to-peer network environments—in which case a server may not be included in a network environment—and one or more client-server network environments—in which case one or more servers may be included in a network environment. In peer-to-peer network environments, functionality described herein with respect to a server(s) may be implemented on any number of client devices.

In at least one embodiment, a network environment may include one or more cloud-based network environments, a distributed computing environment, a combination thereof, etc. A cloud-based network environment may include a framework layer, a job scheduler, a resource manager, and a distributed file system implemented on one or more of servers, which may include one or more core network servers and/or edge servers. A framework layer may include a framework to support software of a software layer and/or one or more application(s) of an application layer. The software or application(s) may respectively include web-based service software or applications. In embodiments, one or more of the client devices may use the web-based service software or applications (e.g., by accessing the service software and/or applications via one or more application programming interfaces (APIs)). The framework layer may be, but is not limited to, a type of free and open-source software web application framework such as that may use a distributed file system for large-scale data processing (e.g., "big data").

A cloud-based network environment may provide cloud computing and/or cloud storage that carries out any combination of computing and/or data storage functions described herein (or one or more portions thereof). Any of these various functions may be distributed over multiple locations from central or core servers (e.g., of one or more data centers that may be distributed across a state, a region, a country, the globe, etc.). If a connection to a user (e.g., a client device) is relatively close to an edge server(s), a core server(s) may designate at least a portion of the functionality to the edge server(s). A cloud-based network environment may be private (e.g., limited to a single organization), may be public (e.g., available to many organizations), and/or a combination thereof (e.g., a hybrid cloud environment).

The client device(s) may include at least some of the components, features, and functionality of the example processing system 500 of FIG. 5A and/or exemplary system 565 of FIG. 5B. By way of example and not limitation, a client device may be embodied as a Personal Computer (PC), a laptop computer, a mobile device, a smartphone, a tablet computer, a smart watch, a wearable computer, a Personal Digital Assistant (PDA), an MP3 player, a virtual reality headset, a Global Positioning System (GPS) or device, a video player, a video camera, a surveillance device or system, a vehicle, a boat, a flying vessel, a virtual machine, a drone, a robot, a handheld communications device, a hospital device, a gaming device or system, an entertainment system, a vehicle computer system, an embedded system controller, a remote control, an appliance, a consumer electronic device, a workstation, an edge device, any combination of these delineated devices, or any other suitable device.

Machine Learning

Deep neural networks (DNNs) developed on processors, such as the PPU 400 have been used for diverse use cases, from self-driving cars to faster drug development, from automatic image captioning in online image databases to smart real-time language translation in video chat applications. Deep learning is a technique that models the neural learning process of the human brain, continually learning, continually getting smarter, and delivering more accurate results more quickly over time. A child is initially taught by an adult to correctly identify and classify various shapes, eventually being able to identify shapes without any coaching. Similarly, a deep learning or neural learning system needs to be trained in object recognition and classification for it get smarter and more efficient at identifying basic objects, occluded objects, etc., while also assigning context to objects.

At the simplest level, neurons in the human brain look at various inputs that are received, importance levels are assigned to each of these inputs, and output is passed on to other neurons to act upon. An artificial neuron or perceptron is the most basic model of a neural network. In one example, a perceptron may receive one or more inputs that represent various features of an object that the perceptron is being trained to recognize and classify, and each of these features is assigned a certain weight based on the importance of that feature in defining the shape of an object.

A deep neural network (DNN) model includes multiple layers of many connected nodes (e.g., perceptrons, Boltzmann machines, radial basis functions, convolutional layers, etc.) that can be trained with enormous amounts of input data to quickly solve complex problems with high accuracy. In one example, a first layer of the DNN model breaks down an input image of an automobile into various sections and looks for basic patterns such as lines and angles. The second layer assembles the lines to look for higher level patterns such as wheels, windshields, and mirrors. The next layer identifies the type of vehicle, and the final few layers generate a label for the input image, identifying the model of a specific automobile brand.

Once the DNN is trained, the DNN can be deployed and used to identify and classify objects or patterns in a process known as inference. Examples of inference (the process through which a DNN extracts useful information from a given input) include identifying handwritten numbers on checks deposited into ATM machines, identifying images of friends in photos, delivering movie recommendations to over fifty million users, identifying and classifying different types of automobiles, pedestrians, and road hazards in driverless cars, or translating human speech in real-time.

During training, data flows through the DNN in a forward propagation phase until a prediction is produced that indicates a label corresponding to the input. If the neural network does not correctly label the input, then errors between the correct label and the predicted label are analyzed, and the weights are adjusted for each feature during a backward propagation phase until the DNN correctly labels the input and other inputs in a training dataset. Training complex neural networks requires massive amounts of parallel computing performance, including floating-point multiplications and additions that are supported by the PPU 400. Inferencing is less compute-intensive than training, being a latency-sensitive process where a trained neural network is applied to new inputs it has not seen before to classify images, detect emotions, identify recommendations, recognize and translate speech, and generally infer new information.

Neural networks rely heavily on matrix math operations, and complex multi-layered networks require tremendous amounts of floating-point performance and bandwidth for both efficiency and speed. With thousands of processing cores, optimized for matrix math operations, and delivering tens to hundreds of TFLOPS of performance, the PPU 400 is a computing platform capable of delivering performance required for deep neural network-based artificial intelligence and machine learning applications.

Furthermore, images generated applying one or more of the techniques disclosed herein may be used to train, test, or certify DNNs used to recognize objects and environments in the real world. Such images may include scenes of roadways, factories, buildings, urban settings, rural settings, humans, animals, and any other physical object or real-world setting. Such images may be used to train, test, or certify DNNs that are employed in machines or robots to manipulate, handle, or modify physical objects in the real world. Furthermore, such images may be used to train, test, or certify DNNs that are employed in autonomous vehicles to navigate and move the vehicles through the real world. Additionally, images generated applying one or more of the techniques disclosed herein may be used to convey information to users of such machines, robots, and vehicles.

Figure 5C:
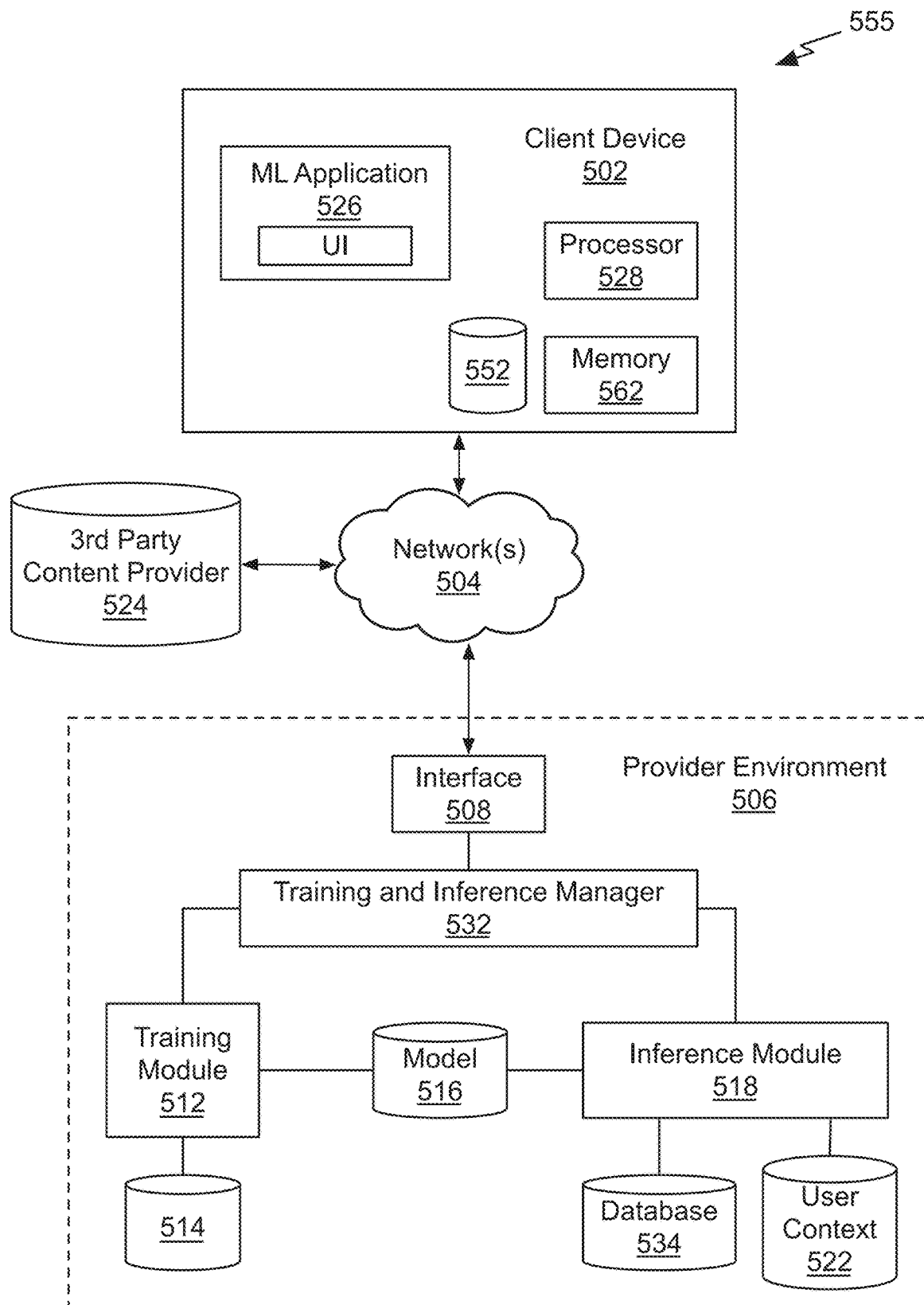
FIG. 5C illustrates components of an exemplary system that can be used to train and utilize machine learning, in at least one embodiment.

FIG. 5C illustrates components of an exemplary system 555 that can be used to train and utilize machine learning, in accordance with at least one embodiment. As will be discussed, various components can be provided by various combinations of computing devices and resources, or a single computing system, which may be under control of a single entity or multiple entities. Further, aspects may be triggered, initiated, or requested by different entities. In at least one embodiment training of a neural network might be instructed by a provider associated with provider environment 506, while in at least one embodiment training might be requested by a customer or other user having access to a provider environment through a client device 502 or other such resource. In at least one embodiment, training data (or data to be analyzed by a trained neural network) can be provided by a provider, a user, or a third party content provider 524. In at least one embodiment, client device 502 may be a vehicle or object that is to be navigated on behalf of a user, for example, which can submit requests and/or receive instructions that assist in navigation of a device.

In at least one embodiment, requests are able to be submitted across at least one network 504 to be received by a provider environment 506. In at least one embodiment, a client device may be any appropriate electronic and/or computing devices enabling a user to generate and send such requests, such as, but not limited to, desktop computers, notebook computers, computer servers, smartphones, tablet computers, gaming consoles (portable or otherwise), computer processors, computing logic, and set-top boxes. Network(s) 504 can include any appropriate network for transmitting a request or other such data, as may include Internet, an intranet, an Ethernet, a cellular network, a local area network (LAN), a wide area network (WAN), a personal area network (PAN), an ad hoc network of direct wireless connections among peers, and so on.

In at least one embodiment, requests can be received at an interface layer 508, which can forward data to a training and inference manager 532, in this example. The training and inference manager 532 can be a system or service including hardware and software for managing requests and service corresponding data or content, in at least one embodiment, the training and inference manager 532 can receive a request to train a neural network, and can provide data for a request to a training module 512. In at least one embodiment, training module 512 can select an appropriate model or neural network to be used, if not specified by the request, and can train a model using relevant training data. In at least one embodiment, training data can be a batch of data stored in a training data repository 514, received from client device 502, or obtained from a third party provider 524. In at least one embodiment, training module 512 can be responsible for training data. A neural network can be any appropriate network, such as a recurrent neural network (RNN) or convolutional neural network (CNN). Once a neural network is trained and successfully evaluated, a trained neural network can be stored in a model repository 516, for example, that may store different models or networks for users, applications, or services, etc. In at least one embodiment, there may be multiple models for a single application or entity, as may be utilized based on a number of different factors.

In at least one embodiment, at a subsequent point in time, a request may be received from client device 502 (or another such device) for content (e.g., path determinations) or data that is at least partially determined or impacted by a trained neural network. This request can include, for example, input data to be processed using a neural network to obtain one or more inferences or other output values, classifications, or predictions, or for at least one embodiment, input data can be received by interface layer 508 and directed to inference module 518, although a different system or service can be used as well. In at least one embodiment, inference module 518 can obtain an appropriate trained network, such as a trained deep neural network (DNN) as discussed herein, from model repository 516 if not already stored locally to inference module 518. Inference module 518 can provide data as input to a trained network, which can then generate one or more inferences as output. This may include, for example, a classification of an instance of input data. In at least one embodiment, inferences can then be transmitted to client device 502 for display or other communication to a user. In at least one embodiment, context data for a user may also be stored to a user context data repository 522, which may include data about a user which may be useful as input to a network in generating inferences, or determining data to return to a user after obtaining instances. In at least one embodiment, relevant data, which may include at least some of input or inference data, may also be stored to a local database 534 for processing future requests. In at least one embodiment, a user can use account information or other information to access resources or functionality of a provider environment. In at least one embodiment, if permitted and available, user data may also be collected and used to further train models, in order to provide more accurate inferences for future requests. In at least one embodiment, requests may be received through a user interface to a machine learning application 526 executing on client device 502, and results displayed through a same interface. A client device can include resources such as a processor 528 and memory 562 for generating a request and processing results or a response, as well as at least one data storage element 552 for storing data for machine learning application 526.

In at least one embodiment a processor 528 (or a processor of training module 512 or inference module 518) will be a central processing unit (CPU). As mentioned, however, resources in such environments can utilize GPUs to process data for at least certain types of requests. With thousands of cores, GPUs, such as PPU 300 are designed to handle substantial parallel workloads and, therefore, have become popular in deep learning for training neural networks and generating predictions. While use of GPUs for offline builds has enabled faster training of larger and more complex models, generating predictions offline implies that either request-time input features cannot be used or predictions must be generated for all permutations of features and stored in a lookup table to serve real-time requests. If a deep learning framework supports a CPU-mode and a model is small and simple enough to perform a feed-forward on a CPU with a reasonable latency, then a service on a CPU instance could host a model. In this case, training can be done offline on a GPU and inference done in real-time on a CPU. If a CPU approach is not viable, then a service can run on a GPU instance. Because GPUs have different performance and cost characteristics than CPUs, however, running a service that offloads a runtime algorithm to a GPU can require it to be designed differently from a CPU based service.

In at least one embodiment, video data can be provided from client device 502 for enhancement in provider environment 506. In at least one embodiment, video data can be processed for enhancement on client device 502. In at least one embodiment, video data may be streamed from a third party content provider 524 and enhanced by third party content provider 524, provider environment 506, or client device 502. In at least one embodiment, video data can be provided from client device 502 for use as training data in provider environment 506.

In at least one embodiment, supervised and/or unsupervised training can be performed by the client device 502 and/or the provider environment 506. In at least one embodiment, a set of training data 514 (e.g., classified or labeled data) is provided as input to function as training data. In at least one embodiment, training data can include instances of at least one type of object for which a neural network is to be trained, as well as information that identifies that type of object. In at least one embodiment, training data might include a set of images that each includes a representation of a type of object, where each image also includes, or is associated with, a label, metadata, classification, or other piece of information identifying a type of object represented in a respective image. Various other types of data may be used as training data as well, as may include text data, audio data, video data, and so on. In at least one embodiment, training data 514 is provided as training input to a training module 512. In at least one embodiment, training module 512 can be a system or service that includes hardware and software, such as one or more computing devices executing a training application, for training a neural network (or other model or algorithm, etc.). In at least one embodiment, training module 512 receives an instruction or request indicating a type of model to be used for training, in at least one embodiment, a model can be any appropriate statistical model, network, or algorithm useful for such purposes, as may include an artificial neural network, deep learning algorithm, learning classifier, Bayesian network, and so on. In at least one embodiment, training module 512 can select an initial model, or other untrained model, from an appropriate repository 516 and utilize training data 514 to train a model, thereby generating a trained model (e.g., trained deep neural network) that can be used to classify similar types of data, or generate other such inferences. In at least one embodiment where training data is not used, an appropriate initial model can still be selected for training on input data per training module 512.

In at least one embodiment, a model can be trained in a number of different ways, as may depend in part upon a type of model selected. In at least one embodiment, a machine learning algorithm can be provided with a set of training data, where a model is a model artifact created by a training process. In at least one embodiment, each instance of training data contains a correct answer (e.g., classification), which can be referred to as a target or target attribute. In at least one embodiment, a learning algorithm finds patterns in training data that map input data attributes to a target, an answer to be predicted, and a machine learning model is output that captures these patterns. In at least one embodiment, a machine learning model can then be used to obtain predictions on new data for which a target is not specified.

In at least one embodiment, training and inference manager 532 can select from a set of machine learning models including binary classification, multiclass classification, generative, and regression models. In at least one embodiment, a type of model to be used can depend at least in part upon a type of target to be predicted.

Graphics Processing Pipeline

In an embodiment, the PPU 400 comprises a graphics processing unit (GPU). The PPU 400 is configured to receive commands that specify shader programs for processing graphics data. Graphics data may be defined as a set of primitives such as points, lines, triangles, quads, triangle strips, and the like. Typically, a primitive includes data that specifies a number of vertices for the primitive (e.g., in a model-space coordinate system) as well as attributes associated with each vertex of the primitive. The PPU 400 can be configured to process the graphics primitives to generate a frame buffer (e.g., pixel data for each of the pixels of the display).

An application writes model data for a scene (e.g., a collection of vertices and attributes) to a memory such as a system memory or memory 404. The model data defines each of the objects that may be visible on a display. The application then makes an API call to the driver kernel that requests the model data to be rendered and displayed. The driver kernel reads the model data and writes commands to the one or more streams to perform operations to process the model data. The commands may reference different shader programs to be implemented on the processing units within the PPU 400 including one or more of a vertex shader, hull shader, domain shader, geometry shader, and a pixel shader. For example, one or more of the processing units may be configured to execute a vertex shader program that processes a number of vertices defined by the model data. In an embodiment, the different processing units may be configured to execute different shader programs concurrently. For example, a first subset of processing units may be configured to execute a vertex shader program while a second subset of processing units may be configured to execute a pixel shader program. The first subset of processing units processes vertex data to produce processed vertex data and writes the processed vertex data to the L2 cache 460 and/or the memory 404. After the processed vertex data is rasterized (e.g., transformed from three-dimensional data into two-dimensional data in screen space) to produce fragment data, the second subset of processing units executes a pixel shader to produce processed fragment data, which is then blended with other processed fragment data and written to the frame buffer in memory 404. The vertex shader program and pixel shader program may execute concurrently, processing different data from the same scene in a pipelined fashion until all of the model data for the scene has been rendered to the frame buffer. Then, the contents of the frame buffer are transmitted to a display controller for display on a display device.

Figure 6A:
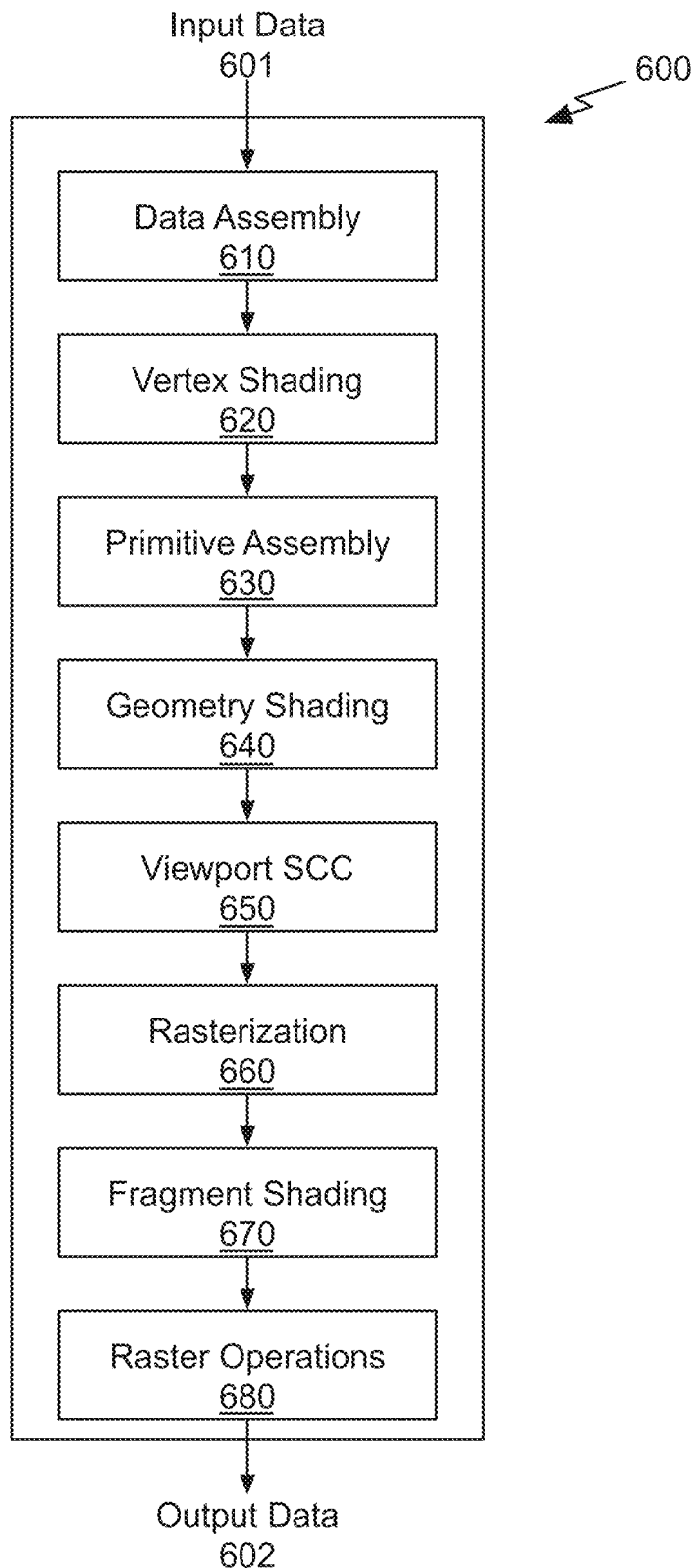
FIG. 6A is a conceptual diagram of a graphics processing pipeline implemented by the PPU of FIG. 4 suitable for use in implementing some embodiments of the present disclosure.

FIG. 6A is a conceptual diagram of a graphics processing pipeline 600 implemented by the PPU 400 of FIG. 4, in accordance with an embodiment. The graphics processing pipeline 600 is an abstract flow diagram of the processing steps implemented to generate 2D computer-generated images from 3D geometry data. As is well-known, pipeline architectures may perform long latency operations more efficiently by splitting up the operation into a plurality of stages, where the output of each stage is coupled to the input of the next successive stage. Thus, the graphics processing pipeline 600 receives input data 601 that is transmitted from one stage to the next stage of the graphics processing pipeline 600 to generate output data 602. In an embodiment, the graphics processing pipeline 600 may represent a graphics processing pipeline defined by the OpenGL® API. As an option, the graphics processing pipeline 600 may be implemented in the context of the functionality and architecture of the previous Figures and/or any subsequent Figure(s).

As shown in FIG. 6A, the graphics processing pipeline 600 comprises a pipeline architecture that includes a number of stages. The stages include, but are not limited to, a data assembly stage 610, a vertex shading stage 620, a primitive assembly stage 630, a geometry shading stage 640, a viewport scale, cull, and clip (VSCC) stage 650, a rasterization stage 660, a fragment shading stage 670, and a raster operations stage 680. In an embodiment, the input data 601 comprises commands that configure the processing units to implement the stages of the graphics processing pipeline 600 and geometric primitives (e.g., points, lines, triangles, quads, triangle strips or fans, etc.) to be processed by the stages. The output data 602 may comprise pixel data (e.g., color data) that is copied into a frame buffer or other type of surface data structure in a memory.

The data assembly stage 610 receives the input data 601 that specifies vertex data for high-order surfaces, primitives, or the like. The data assembly stage 610 collects the vertex data in a temporary storage or queue, such as by receiving a command from the host processor that includes a pointer to a buffer in memory and reading the vertex data from the buffer. The vertex data is then transmitted to the vertex shading stage 620 for processing.

The vertex shading stage 620 processes vertex data by performing a set of operations (e.g., a vertex shader or a program) once for each of the vertices. Vertices may be, e.g., specified as a 4-coordinate vector (e.g., <x, y, z, w>) associated with one or more vertex attributes (e.g., color, texture coordinates, surface normal, etc.). The vertex shading stage 620 may manipulate individual vertex attributes such as position, color, texture coordinates, and the like. In other words, the vertex shading stage 620 performs operations on the vertex coordinates or other vertex attributes associated with a vertex. Such operations commonly including lighting operations (e.g., modifying color attributes for a vertex) and transformation operations (e.g., modifying the coordinate space for a vertex). For example, vertices may be specified using coordinates in an object-coordinate space, which are transformed by multiplying the coordinates by a matrix that translates the coordinates from the object-coordinate space into a world space or a normalized-device-coordinate (NCD) space. The vertex shading stage 620 generates transformed vertex data that is transmitted to the primitive assembly stage 630.

The primitive assembly stage 630 collects vertices output by the vertex shading stage 620 and groups the vertices into geometric primitives for processing by the geometry shading stage 640. For example, the primitive assembly stage 630 may be configured to group every three consecutive vertices as a geometric primitive (e.g., a triangle) for transmission to the geometry shading stage 640. In some embodiments, specific vertices may be reused for consecutive geometric primitives (e.g., two consecutive triangles in a triangle strip may share two vertices). The primitive assembly stage 630 transmits geometric primitives (e.g., a collection of associated vertices) to the geometry shading stage 640.

The geometry shading stage 640 processes geometric primitives by performing a set of operations (e.g., a geometry shader or program) on the geometric primitives. Tessellation operations may generate one or more geometric primitives from each geometric primitive. In other words, the geometry shading stage 640 may subdivide each geometric primitive into a finer mesh of two or more geometric primitives for processing by the rest of the graphics processing pipeline 600. The geometry shading stage 640 transmits geometric primitives to the viewport SCC stage 650.

In an embodiment, the graphics processing pipeline 600 may operate within a streaming multiprocessor and the vertex shading stage 620, the primitive assembly stage 630, the geometry shading stage 640, the fragment shading stage 670, and/or hardware/software associated therewith, may sequentially perform processing operations. Once the sequential processing operations are complete, in an embodiment, the viewport SCC stage 650 may utilize the data. In an embodiment, primitive data processed by one or more of the stages in the graphics processing pipeline 600 may be written to a cache (e.g. L1 cache, a vertex cache, etc.). In this case, in an embodiment, the viewport SCC stage 650 may access the data in the cache. In an embodiment, the viewport SCC stage 650 and the rasterization stage 660 are implemented as fixed function circuitry.

The viewport SCC stage 650 performs viewport scaling, culling, and clipping of the geometric primitives. Each surface being rendered to is associated with an abstract camera position. The camera position represents a location of a viewer looking at the scene and defines a viewing frustum that encloses the objects of the scene. The viewing frustum may include a viewing plane, a rear plane, and four clipping planes. Any geometric primitive entirely outside of the viewing frustum may be culled (e.g., discarded) because the geometric primitive will not contribute to the final rendered scene. Any geometric primitive that is partially inside the viewing frustum and partially outside the viewing frustum may be clipped (e.g., transformed into a new geometric primitive that is enclosed within the viewing frustum. Furthermore, geometric primitives may each be scaled based on a depth of the viewing frustum. All potentially visible geometric primitives are then transmitted to the rasterization stage 660.

The rasterization stage 660 converts the 3D geometric primitives into 2D fragments (e.g. capable of being utilized for display, etc.). The rasterization stage 660 may be configured to utilize the vertices of the geometric primitives to setup a set of plane equations from which various attributes can be interpolated. The rasterization stage 660 may also compute a coverage mask for a plurality of pixels that indicates whether one or more sample locations for the pixel intercept the geometric primitive. In an embodiment, z-testing may also be performed to determine if the geometric primitive is occluded by other geometric primitives that have already been rasterized. The rasterization stage 660 generates fragment data (e.g., interpolated vertex attributes associated with a particular sample location for each covered pixel) that are transmitted to the fragment shading stage 670.

The fragment shading stage 670 processes fragment data by performing a set of operations (e.g., a fragment shader or a program) on each of the fragments. The fragment shading stage 670 may generate pixel data (e.g., color values) for the fragment such as by performing lighting operations or sampling texture maps using interpolated texture coordinates for the fragment. The fragment shading stage 670 generates pixel data that is transmitted to the raster operations stage 680.

The raster operations stage 680 may perform various operations on the pixel data such as performing alpha tests, stencil tests, and blending the pixel data with other pixel data corresponding to other fragments associated with the pixel. When the raster operations stage 680 has finished processing the pixel data (e.g., the output data 602), the pixel data may be written to a render target such as a frame buffer, a color buffer, or the like.

It will be appreciated that one or more additional stages may be included in the graphics processing pipeline 600 in addition to or in lieu of one or more of the stages described above. Various implementations of the abstract graphics processing pipeline may implement different stages. Furthermore, one or more of the stages described above may be excluded from the graphics processing pipeline in some embodiments (such as the geometry shading stage 640). Other types of graphics processing pipelines are contemplated as being within the scope of the present disclosure. Furthermore, any of the stages of the graphics processing pipeline 600 may be implemented by one or more dedicated hardware units within a graphics processor such as PPU 400. Other stages of the graphics processing pipeline 600 may be implemented by programmable hardware units such as the processing unit within the PPU 400.

The graphics processing pipeline 600 may be implemented via an application executed by a host processor, such as a CPU. In an embodiment, a device driver may implement an application programming interface (API) that defines various functions that can be utilized by an application in order to generate graphical data for display. The device driver is a software program that includes a plurality of instructions that control the operation of the PPU 400. The API provides an abstraction for a programmer that lets a programmer utilize specialized graphics hardware, such as the PPU 400, to generate the graphical data without requiring the programmer to utilize the specific instruction set for the PPU 400. The application may include an API call that is routed to the device driver for the PPU 400. The device driver interprets the API call and performs various operations to respond to the API call. In some instances, the device driver may perform operations by executing instructions on the CPU. In other instances, the device driver may perform operations, at least in part, by launching operations on the PPU 400 utilizing an input/output interface between the CPU and the PPU 400. In an embodiment, the device driver is configured to implement the graphics processing pipeline 600 utilizing the hardware of the PPU 400.

Various programs may be executed within the PPU 400 in order to implement the various stages of the graphics processing pipeline 600. For example, the device driver may launch a kernel on the PPU 400 to perform the vertex shading stage 620 on one processing unit (or multiple processing units). The device driver (or the initial kernel executed by the PPU 400) may also launch other kernels on the PPU 400 to perform other stages of the graphics processing pipeline 600, such as the geometry shading stage 640 and the fragment shading stage 670. In addition, some of the stages of the graphics processing pipeline 600 may be implemented on fixed unit hardware such as a rasterizer or a data assembler implemented within the PPU 400. It will be appreciated that results from one kernel may be processed by one or more intervening fixed function hardware units before being processed by a subsequent kernel on a processing unit.

Images generated applying one or more of the techniques disclosed herein may be displayed on a monitor or other display device. In some embodiments, the display device may be coupled directly to the system or processor generating or rendering the images. In other embodiments, the display device may be coupled indirectly to the system or processor such as via a network. Examples of such networks include the Internet, mobile telecommunications networks, a WIFI network, as well as any other wired and/or wireless networking system. When the display device is indirectly coupled, the images generated by the system or processor may be streamed over the network to the display device. Such streaming allows, for example, video games or other applications, which render images, to be executed on a server, a data center, or in a cloud-based computing environment and the rendered images to be transmitted and displayed on one or more user devices (such as a computer, video game console, smartphone, other mobile device, etc.) that are physically separate from the server or data center. Hence, the techniques disclosed herein can be applied to enhance the images that are streamed and to enhance services that stream images such as NVIDIA GeForce Now (GFN), Google Stadia, and the like.

Example Streaming System

Figure 6B:
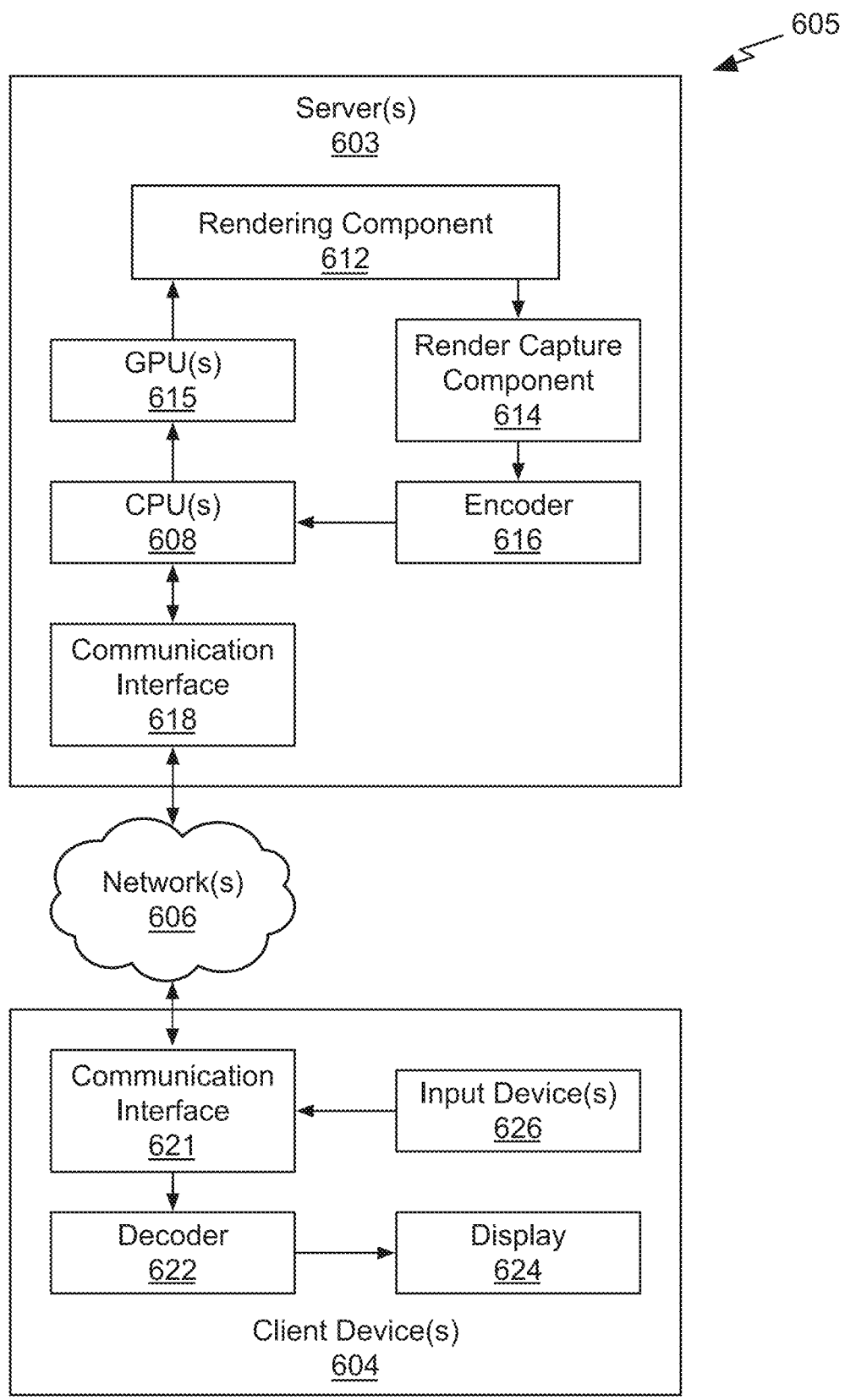
FIG. 6B illustrates an exemplary streaming system suitable for use in implementing some embodiments of the present disclosure.

FIG. 6B is an example system diagram for a streaming system 605, in accordance with some embodiments of the present disclosure. FIG. 6B includes server(s) 603 (which may include similar components, features, and/or functionality to the example processing system 500 of FIG. 5A and/or exemplary system 565 of FIG. 5B), client device(s) 604 (which may include similar components, features, and/or functionality to the example processing system 500 of FIG. 5A and/or exemplary system 565 of FIG. 5B), and network(s) 606 (which may be similar to the network(s) described herein). In some embodiments of the present disclosure, the system 605 may be implemented.

In an embodiment, the streaming system 605 is a game streaming system and the sever(s) 604 are game server(s). In the system 605, for a game session, the client device(s) 604 may only receive input data in response to inputs to the input device(s) 626, transmit the input data to the server(s) 603, receive encoded display data from the server(s) 603, and display the display data on the display 624. As such, the more computationally intense computing and processing is offloaded to the server(s) 603 (e.g., rendering—in particular ray or path tracing—for graphical output of the game session is executed by the GPU(s) 615 of the server(s) 603). In other words, the game session is streamed to the client device(s) 604 from the server(s) 603, thereby reducing the requirements of the client device(s) 604 for graphics processing and rendering.

For example, with respect to an instantiation of a game session, a client device 604 may be displaying a frame of the game session on the display 624 based on receiving the display data from the server(s) 603. The client device 604 may receive an input to one of the input device(s) 626 and generate input data in response. The client device 604 may transmit the input data to the server(s) 603 via the communication interface 621 and over the network(s) 606 (e.g., the Internet), and the server(s) 603 may receive the input data via the communication interface 618. The CPU(s) 608 may receive the input data, process the input data, and transmit data to the GPU(s) 615 that causes the GPU(s) 615 to generate a rendering of the game session. For example, the input data may be representative of a movement of a character of the user in a game, firing a weapon, reloading, passing a ball, turning a vehicle, etc. The rendering component 612 may render the game session (e.g., representative of the result of the input data) and the render capture component 614 may capture the rendering of the game session as display data (e.g., as image data capturing the rendered frame of the game session). The rendering of the game session may include ray or path-traced lighting and/or shadow effects, computed using one or more parallel processing units—such as GPUs, which may further employ the use of one or more dedicated hardware accelerators or processing cores to perform ray or path-tracing techniques—of the server(s) 603. The encoder 616 may then encode the display data to generate encoded display data and the encoded display data may be transmitted to the client device 604 over the network(s) 606 via the communication interface 618. The client device 604 may receive the encoded display data via the communication interface 621 and the decoder 622 may decode the encoded display data to generate the display data. The client device 604 may then display the display data via the display 624.

It is noted that the techniques described herein may be embodied in executable instructions stored in a computer readable medium for use by or in connection with a processor-based instruction execution machine, system, apparatus, or device. It will be appreciated by those skilled in the art that, for some embodiments, various types of computer-readable media can be included for storing data. As used herein, a "computer-readable medium" includes one or more of any suitable media for storing the executable instructions of a computer program such that the instruction execution machine, system, apparatus, or device may read (or fetch) the instructions from the computer-readable medium and execute the instructions for carrying out the described embodiments. Suitable storage formats include one or more of an electronic, magnetic, optical, and electromagnetic format. A non-exhaustive list of conventional exemplary computer-readable medium includes: a portable computer diskette; a random-access memory (RAM); a read-only memory (ROM); an erasable programmable read only memory (EPROM); a flash memory device; and optical storage devices, including a portable compact disc (CD), a portable digital video disc (DVD), and the like.

It should be understood that the arrangement of components illustrated in the attached Figures are for illustrative purposes and that other arrangements are possible. For example, one or more of the elements described herein may be realized, in whole or in part, as an electronic hardware component. Other elements may be implemented in software, hardware, or a combination of software and hardware. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

To facilitate an understanding of the subject matter described herein, many aspects are described in terms of sequences of actions. It will be recognized by those skilled in the art that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

What is claimed is:

1. A computer-implemented method, comprising:
    processing tomography images by a first neural network to produce at least one channel of two-dimensional (2D) features for each tomography image;
    based on properties of a voxel grid, projecting a three-dimensional (3D) distribution onto a detector to produce a projected 2D distribution at the detector;
    calculating a 2D footprint based on the projected 2D distribution;
    computing 3D features by sampling the at least one channel of 2D features for the tomography images according to the 2D footprint; and
    processing the 3D features by a second neural network to produce a 3D density volume corresponding to the tomography images.

2. The computer-implemented method of claim 1, wherein noise present in the tomography images is reduced in the 3D density volume.

3. The computer-implemented method of claim 1, wherein the 3D features are voxels and associated attributes and the 3D features are generated in parallel for at least a portion of the voxels.

4. The computer-implemented method of claim 1, wherein the 3D density volume corresponds to a portion of a human body.

5. The computer-implemented method of claim 1, wherein a physical environment used to capture the tomography images comprises a conical spiral computerized tomography machine.

6. The computer-implemented method of claim 1, wherein the sampling includes accessing one or more prefiltered versions of the tomography images according to at least one dimension of the 2D footprint.

7. The computer-implemented method of claim 1, further comprising training at least one of the first neural network and the second neural network without ground truth reference data by:
    projecting the 3D density volume according to an environment used to capture the tomography images to produce reference tomography images corresponding to the tomography images; and
    adjusting parameters of at least one of the first neural network and the second neural network to reduce differences between the reference tomography images and the tomography images.

8. The computer-implemented method of claim 1, wherein at least one of the steps of processing the tomography images, computing, and processing the 3D features are performed on a server or in a data center and the 3D density volume is streamed to a user device.

9. The computer-implemented method of claim 1, wherein at least one of the steps of processing the tomography images, computing, and processing the 3D features are performed within a cloud computing environment.

10. The computer-implemented method of claim 1, wherein at least one of the steps of processing the tomography images, computing, and processing the 3D features are performed for training, testing, or certifying a neural network employed in a machine, robot, or autonomous vehicle.

11. The computer-implemented method of claim 1, wherein at least one of the steps of processing the tomography images, computing, and processing the 3D features is performed on a virtual machine comprising a portion of a graphics processing unit.

12. The computer-implemented method of claim 1, wherein the 3D distribution is determined based on at least one of resolution of the input tomography images, voxel spacing, and characteristics of the detector.

13. A system, comprising:
    a memory that stores tomography images;
    a processor that is connected to the memory, wherein the processor is configured to produce a three-dimensional (3D) density volume corresponding to the tomography images by:
    executing a first neural network to produce at least one channel of two-dimensional (2D) features for each tomography image;
    based on properties of a voxel grid, projecting a 3D distribution onto a detector to produce a projected 2D distribution at the detector;
    calculating a 2D footprint based on the projected 2D distribution;
    computing 3D features by sampling the at least one channel of 2D features for the tomography images according to the 2D footprint; and
    executing a second neural network to process the 3D features and produce the 3D density volume corresponding to the tomography images.

14. The system of claim 13, wherein noise present in the tomography images is reduced in the 3D density volume.

15. The system of claim 13, wherein 3D features are voxels and associated attributes and the 3D features are generated in parallel for at least a portion of the voxels.

16. The system of claim 13, wherein 3D density volume corresponds to a portion of a human body.

17. The system of claim 13, wherein the sampling includes accessing one or more prefiltered versions of the tomography images according to at least one dimension of the 2D footprint.

18. The system of claim 13, further comprising training at least one of the first neural network and the second neural network without ground truth reference data by:
- projecting the 3D density volume according to an environment used to capture the tomography images to produce reference tomography images corresponding to the tomography images; and
- adjusting parameters of at least one of the first neural network and the second neural network to reduce differences between the reference tomography images and the tomography images.

19. A non-transitory computer-readable media storing computer instructions that, when executed by one or more processors, cause the one or more processors to perform the steps of:
- processing tomography images by a first neural network to produce at least one channel of two-dimensional (2D) features for each tomography image;
- based on properties of a voxel grid, projecting a three-dimensional distribution onto a detector to produce a projected 2D distribution at the detector;
- calculating a 2D footprint based on the projected 2D distribution;
- computing three-dimensional (3D) features by sampling the at least one channel of 2D features for the tomography images according to the 2D footprint; and
- processing the 3D features by a second neural network to produce a 3D density volume corresponding to the tomography images.

20. The non-transitory computer-readable media of claim 19, wherein the sampling includes accessing one or more prefiltered versions of the tomography images according to at least one dimension of the 2D footprint.

* * * * *